US010259819B2

(12) United States Patent
Chapman et al.

(10) Patent No.: US 10,259,819 B2
(45) Date of Patent: Apr. 16, 2019

(54) PROCESS FOR PREPARING OXYCODONE COMPOSITIONS

(71) Applicants: Purdue Pharma L.P., Stamford, CT (US); The P.F. Laboratories, Inc., Totowa, NJ (US); Purdue Pharmaceuticals L.P., Wilson, NC (US); Rhodes Technologies, Coventry, RI (US)

(72) Inventors: Robert Chapman, Downingtown, PA (US); Lonn S. Rider, Foster, RI (US); Qi Hong, Sharon, MA (US); Donald Kyle, Yardley, PA (US); Robert Kupper, East Greenwich, RI (US)

(73) Assignees: PURDUE PHARMA L.P., Stamford, CT (US); THE P.F. LABORATORIES, INC., Totowa, NJ (US); PURDUE PHARMACEUTICALS L.P., Wilson, NC (US); RHODES TECHNOLOGIES, Coventry, RI (US)

( * ) Notice: Subject to any disclaimer, the term of this patent is extended or adjusted under 35 U.S.C. 154(b) by 0 days.

(21) Appl. No.: 15/721,167

(22) Filed: Sep. 29, 2017

(65) Prior Publication Data
US 2018/0022754 A1    Jan. 25, 2018

Related U.S. Application Data

(63) Continuation of application No. 15/058,420, filed on Mar. 2, 2016, now Pat. No. 9,777,011, which is a continuation of application No. 14/725,210, filed on May 29, 2015, now abandoned, which is a continuation of application No. 13/366,755, filed on Feb. 6, 2012, now Pat. No. 9,073,933, which is a continuation of application No. 12/893,681, filed on Sep. 29, 2010, now abandoned, which is a continuation of application No. 12/380,800, filed on Mar. 4, 2009, now abandoned, which is a continuation of application No. 11/635,529, filed on Jan. 16, 2007, now Pat. No. 7,683,072, which is a continuation of application No. 11/391,897, filed on Mar. 29, 2006, which is a continuation of application No. 11/093,626, filed on Mar. 30, 2005, now Pat. No. 7,129,248.

(60) Provisional application No. 60/651,778, filed on Feb. 10, 2005, provisional application No. 60/648,625, filed on Jan. 31, 2005, provisional application No. 60/620,072, filed on Oct. 18, 2004, provisional application No. 60/601,534, filed on Aug. 13, 2004, provisional application No. 60/557,492, filed on Mar. 30, 2004.

(51) Int. Cl.
A61K 31/485 (2006.01)
C07D 489/08 (2006.01)
C07D 489/02 (2006.01)
A61K 9/20 (2006.01)
A61K 9/48 (2006.01)
A61K 9/14 (2006.01)
C07D 489/04 (2006.01)

(52) U.S. Cl.
CPC .............. *C07D 489/08* (2013.01); *A61K 9/14* (2013.01); *A61K 9/20* (2013.01); *A61K 9/2095* (2013.01); *A61K 9/48* (2013.01); *A61K 9/4833* (2013.01); *A61K 31/485* (2013.01); *C07D 489/02* (2013.01); *C07D 489/04* (2013.01)

(58) Field of Classification Search
CPC .......................... A61K 31/485; C07D 489/08
USPC .......................................... 514/282; 546/45
See application file for complete search history.

(56) References Cited

U.S. PATENT DOCUMENTS

| | | | |
|---|---|---|---|
| 1,468,805 | A | 9/1923 | Freund et al. |
| 1,485,673 | A | 3/1924 | Freund et al. |
| 2,806,033 | A | 9/1957 | Lewenstein |
| 3,133,132 | A | 5/1964 | Loeb et al. |
| 3,173,876 | A | 3/1965 | Zobrist |
| 3,276,586 | A | 10/1966 | Rosaen |
| 3,541,005 | A | 11/1970 | Strathmann et al. |
| 3,541,006 | A | 11/1970 | Bixler et al. |
| 3,546,876 | A | 12/1970 | Fokker et al. |
| 3,845,770 | A | 11/1974 | Theeuwes et al. |
| 3,894,026 | A | 7/1975 | Sohar et al. |
| 3,905,981 | A | 9/1975 | Olofson et al. |
| 3,916,899 | A | 11/1975 | Theeuwes et al. |
| 4,045,440 | A | 8/1977 | Rappaport et al. |
| 4,063,064 | A | 12/1977 | Saunders et al. |
| 4,088,864 | A | 5/1978 | Theeuwes et al. |
| 4,160,020 | A | 7/1979 | Ayer et al. |
| 4,200,098 | A | 4/1980 | Ayer et al. |
| 4,272,540 | A | 6/1981 | Razdan et al. |
| 4,285,987 | A | 8/1981 | Ayer et al. |
| 4,370,333 | A | 1/1983 | Ghosh et al. |
| 4,639,520 | A | 1/1987 | Kavka et al. |
| 4,795,813 | A | 1/1989 | Schwartz |
| 4,810,699 | A | 3/1989 | Sabatucci et al. |
| 4,861,598 | A | 8/1989 | Oshlack |
| 4,957,681 | A | 9/1990 | Kimesch et al. |

(Continued)

FOREIGN PATENT DOCUMENTS

| | | |
|---|---|---|
| DE | 286431 | 8/1915 |
| DE | 296 916 | 3/1917 |

(Continued)

OTHER PUBLICATIONS

"10-Hydroxythebaine", Bohumil Proksa, Arch. Pharm. Pharm. Med. Chem. 332, 369-370, 1999.

(Continued)

*Primary Examiner* — Charanjit Aulakh
(74) *Attorney, Agent, or Firm* — Dechert LLP

(57) ABSTRACT

In certain embodiments the invention is directed to a process for preparing an oxycodone hydrochloride composition having less than 25 ppm of 14-hydroxycodeinone.

2 Claims, 5 Drawing Sheets

(56) References Cited

U.S. PATENT DOCUMENTS

| | | | |
|---|---|---|---|
| 5,112,975 | A | 5/1992 | Wallace |
| 5,215,758 | A | 6/1993 | Krishnamurthy |
| 5,266,331 | A | 11/1993 | Oshlack et al. |
| 5,273,760 | A | 12/1993 | Oshlack et al. |
| 5,286,493 | A | 2/1994 | Oshlack et al. |
| 5,324,351 | A | 6/1994 | Oshlack et al. |
| 5,356,467 | A | 10/1994 | Oshlack et al. |
| 5,472,712 | A | 12/1995 | Oshlack et al. |
| 5,508,042 | A | 4/1996 | Oshlack et al. |
| 5,549,912 | A | 8/1996 | Oshlack et al. |
| 5,656,295 | A | 8/1997 | Oshlack et al. |
| 5,869,669 | A | 2/1999 | Huang et al. |
| 5,922,876 | A | 7/1999 | Huang et al. |
| 5,948,788 | A | 9/1999 | Huang et al. |
| 5,952,495 | A | 9/1999 | Huang et al. |
| 6,008,354 | A | 12/1999 | Huang et al. |
| 6,008,355 | A | 12/1999 | Huang et al. |
| 6,013,796 | A | 1/2000 | Huang et al. |
| 6,090,943 | A | 7/2000 | Mudryk et al. |
| 6,177,567 | B1 | 1/2001 | Chiu et al. |
| 6,262,266 | B1 | 7/2001 | Chiu et al. |
| 6,403,798 | B2 | 6/2002 | Chiu et al. |
| 6,710,223 | B1 | 3/2004 | Rijswijck et al. |
| 6,864,370 | B1 | 3/2005 | Lin et al. |
| 7,071,336 | B2 | 7/2006 | Francis et al. |
| 7,129,248 | B2 | 10/2006 | Chapman et al. |
| 7,153,966 | B2 | 12/2006 | Casner et al. |
| 7,674,798 | B2 | 3/2010 | Chapman et al. |
| 7,674,799 | B2 | 3/2010 | Chapman et al. |
| 7,674,800 | B2 | 3/2010 | Chapman et al. |
| 7,683,072 | B2 | 3/2010 | Chapman et al. |
| 8,703,950 | B2 | 4/2014 | Keskeny et al. |
| 9,062,062 | B1 * | 6/2015 | Itov ............... C07D 489/08 |
| 9,073,933 | B2 | 7/2015 | Chapman |
| 2001/0008639 | A1 | 7/2001 | Oshlack et al. |
| 2004/0010000 | A1 | 1/2004 | Ayer et al. |
| 2005/0095291 | A1 | 5/2005 | Oshlack et al. |
| 2006/0111383 | A1 | 5/2006 | Casner et al. |
| 2006/0134422 | A1 | 6/2006 | Chenevier et al. |
| 2006/0173029 | A1 | 8/2006 | Chapman et al. |
| 2007/0117826 | A1 | 5/2007 | Jankikhel et al. |
| 2007/0178830 | A1 | 5/2007 | Chapman et al. |
| 2007/0178831 | A1 | 5/2007 | Chapman et al. |
| 2007/0179169 | A1 | 8/2007 | Chapman et al. |
| 2008/0132703 | A1 | 6/2008 | Cox et al. |
| 2008/0139814 | A1 | 6/2008 | Cox et al. |
| 2010/0152449 | A1 | 6/2010 | Chapman et al. |
| 2011/0144340 | A1 | 6/2011 | Cox et al. |

FOREIGN PATENT DOCUMENTS

| | | |
|---|---|---|
| EP | 0068384 | 5/1983 |
| EP | 9213534 | 8/1992 |
| EP | 0889045 | 1/1999 |
| EP | 0900582 | 3/1999 |
| EP | 0943617 | 9/1999 |
| ES | 8607306 | 3/1985 |
| ES | 2 121 554 | 11/1998 |
| FR | 2850576 | 8/2004 |
| JP | 2001-518444 | 10/2001 |
| JP | 2004-502637 | 1/2004 |
| JP | 2007-531756 | 11/2007 |
| KR | 10-2003-0096342 | 12/2003 |
| SU | 64699 | 5/1945 |
| WO | WO 93/10765 | 6/1993 |
| WO | WO 99/02529 | 1/1999 |
| WO | WO 1999/02529 | 1/1999 |
| WO | WO 01/29047 | 4/2001 |
| WO | WO 2001/029047 | 4/2001 |
| WO | WO2001/29047 | 4/2001 |
| WO | WO2001/29048 | 4/2001 |
| WO | WO2002/087512 | 7/2002 |
| WO | WO2002/087512 | 11/2002 |
| WO | WO2002/100382 | 12/2002 |
| WO | WO 2003/007802 | 1/2003 |
| WO | WO2003/082204 | 10/2003 |
| WO | WO 2003/101384 | 12/2003 |
| WO | WO 2004/016618 | 2/2004 |
| WO | WO 2004/045551 | 6/2004 |
| WO | WO 2004/050025 | 6/2004 |
| WO | WO 2004/082620 | 9/2004 |
| WO | WO 2004/108090 | 12/2004 |
| WO | WO 2005/097801 | 10/2005 |
| WO | WO2005/097801 | 10/2005 |
| WO | WO2006/094672 | 9/2006 |
| WO | WO2006/138020 | 12/2006 |
| WO | WO2007/062184 | 5/2007 |
| WO | WO2007/103105 | 9/2007 |
| WO | WO2008/070656 | 6/2008 |
| WO | WO2009/004491 | 1/2009 |
| WO | WO 2012/003468 | 1/2012 |

OTHER PUBLICATIONS

Coop et al., "Studies into the Direct Oxidation of Codeinone to 14-Hydroxycodeinone", Tetrahedron 55 (1999), pp. 11429-11436.

Grounds of Appeal against Decision to refuse European Patent No. 2314589 dated Jul. 17, 2017.

Korean Office Action corresponding to Korean Application No. 10-2015-7009780 dated Dec. 22, 2017.

Notice of Opposition filed against European Patent No. 2426132, dated Oct. 20, 2016.

Patentee's reply to notices of opposition filed against EP 1730151, dated Jul. 27, 2012.

"General Toxicology," *Alpha beta unsat ketones*, pp. 11-12 (2006).

"Identification and Determination of Impurities in Drugs," 2000, Elsevier, edited by Sandor Gorog.

"Opioid Analgesics" by Alan F. Casy and Robert T. Parfitt, 1986, Plenum Press.

1 r. Carl Moy, *Moy's Walker on Patents* § 4:97, 4$^{th}$ ed. 2006.

2002 Label for Oxycontin®, PDR, 56ed. (2002).

English Translation of the Office Action issued in connection with Ecuadorian Patent Application No. SP-06-6953, Sep. 30, 2015.

Information Diclosure Statement filed in connection with the U.S. Appl. No. 14/725,210 on Dec. 30, 2015.

Office Action issued in connection with Ecuador Application 2014-045713 dated Jan. 15, 2015, including an English translation thereof.

Office Action issued in connection with Japanese Application 2014-045713 dated Mar. 3, 2015, including an English translation thereof.

Official Communication, dated Mar. 16, 2015, in connection with EP 10 011 791.0.

Opposition filed by Opponent 01 on Oct. 26, 2015, against EP Patent 2 305 683.

Opposition filed by Opponent 02 on Oct. 27, 2015, against EP Patent 2 305 683.

Opposition filed by Opponent 03 on Oct. 28, 2015, against EP Patent 2 305 683.

Opposition filed by Opponent 04 on Oct. 28, 2015, against EP Patent 2 305 683.

A Modern Approach to Organic Chemistry, Oxford 1958, J. Packer and J. Vaughan, pp. 139-140.

A. C. Currie et al., Some Reactions of 14-Hydroxycodeine, J. Chemical Soc'y 773 (1960).

A. Kleemann et al., "Pharmaceutical Substances: Syntheses, Patents, Applications", vol. 2: N-Z, 4$^{th}$ edition 2001, publisher Thieme, Stuttgart, p. 1530.

Abstract: Chen, HF et al., "Keton EC50 Values in the Microtox test." *Ecotoxicol Eviron Saf.*, vol. 30., No. 2, pp. 120123 (1995).

Abstract: Cooper, KO et al., "Mutagenicity and toxicity studies of several alpha, beta-unstaturated aldehydes in the *Salmonella typhimurium* mutagenicity assay," *Environ Mutagen*, vol. 9, No. 3, pp. 289-295 (1987).

Abstract: Deininger, C. et al., "Mutagenicity and genotoxicity of ethylvinyl ketone in bacterial tests," *J. Appl. Toxicol.* vol. 10, No. 3., pp. 167-171 (1990).

(56) References Cited

OTHER PUBLICATIONS

Abstract: Eder, E. et al., "Identification and characterization of deoxyguanosine adducts of methyl vinyl ketone and ethyl vinyl ketone. Genotoxicity of the ketones in the SOS Chromotest," Chem Res Toxicol., vol. 4, No. 1 (1991).
Abstract: Eder, E. et al., "Molecular mechanisms of DNA damage initiated by alpha, beta-unsaturated carbonyl compounds as criteria for genotoxicity and mutagenicity," Environ Health Perspect., vol. 88, pp. 99-106, (1990).
Abstract: Eder, E. et al., "Mutagenic properties of allylic and alpha, beta-unsaturated compounds: consideration of alkylating mechanisms," Xenobiotica, vol. 12, No. 12, pp. 831-848 (1982).
Abstract: Eder, E. et al., "The influence of the solvents DMSO and ethanol on the genotoxicity of alpha, beta-unsaturated aldehydes in the SOS chromotest," Mutat Res, vol. 516, Nos. 1-2, pp. 81-89 (2002).
Abstract: Eder, E. et al., "The possible role of alpha, beta-unsaturated carbonyl compounds in mutagenesis and carcinogenesis," Toxicol Lett, vol. 67, Nos. 1-3, pp. 87-103 (1993).
Abstract: Eder, E. et al., "The role of alcohols as solvents in the genotoxicity testing of alpha, beta-unsaturated ketones in the SOS chromotest," Mutat Res., vol. 470, No. 1, pp. 29-37 (2000).
Abstract: Hitosugi, N. et al., "Analysis of Opioids as Inducer of Apoptosis in Human Tumor Cells," Anesthesiology, vol. 96 (2002).
Abstract: Hitosugi, N. et al., "Comparative analysis of apoptosis-inducing activity of codeine and codeinone," Anesthesiology, vol. 98, No. 3, pp. 643-650 (2003).
Abstract: Hitosugi, N. et al., "Detection of Apoptosis Signaling Pathway in Human Cancer Cell Lines by Codeinone, a Toxic Metabolite of Codeine," Anesthesiology, vol. 99 (2003).
Abstract: Kawase, M. et al., "Cell death-inducing activity of opiates in human oral tumor cell lines," Anticancer Res., vol. 22, No. 1A, pp. 211-214 (2002).
Abstract: Nagamatsu, K. et al., "Effects of glutathione and Phenobarbital on the toxicity of codeinone," Biochem Pharmacol, vol. 35, No. 10, pp. 1675-1678 (1986).
Abstract: O'Neal, CL et al., "Acetylcodeine, an impurity of illicitly manufactured heroin, elicits convulsions, antinociception, and locomotor stimulation in mice," Drug Alcohol Depend., vol. 65, No. 1, pp. 37-43 (2001).
Abstract: Schultz, TW et al., "Trends in structure-toxicity relationships for carbonyl-containing alpha, beta-unsaturated compounds," SAR QSAR Environ Res., vol. 15, No. 2, pp. 139-146 (2004).
Access to Chemistry, The Royal Society of Chemistry 1999, Chapter 3.3.4, "Neutralisation of Acids", p. 109.
Ackerman, et al., "Patient-Reported Utilization Patterns of Fentanyl Transdermal System and Oxycodone Hydrchloride Controlled-Release Among Patients with Chronic Nonmalignant Pain," Journal of Managed Care Pharmacy, vol. 9, No. 3 (2003), p. 223-231.
Actavis Elizabeth LLC's Answer and Counterclaims, Purdue Pharma L.P. et al. v. Ranbaxy Inc., et al., C.A. No. 10-03734-SHS (SDNY 2010).
Amneal's Notice of Paragraph IV Certification dated Sep. 27, 2011.
An English translation of Auterhoff, et al., pp. 420-428 (1994).
An English translation of Freund and Speyer, pp. 135-178 (1917).
Anand N., Bindra, J. S., Ranganathan, S. Art in Organic Synthesis, John Wiley & Sons, Inc., pp. 50-56, 10913, 127-133, 158-164, 278-286, 375-386 (1970).
Andrew Streitwieser et al., Stereoisomerism, in Introduction to Organic Chemistry 123 (4th ed. 1992).
Answer by Plaintiff/Counterclaim Defendant Grunenthal Gmbh to the First Amended Counterclaims of Defendant Teva Pharmaceuticals, Inc., C.A. No. 1:11-cv-2037-SHS (SDNY 2011).
Answer by Plaintiff/Counterclaim-Defendant Grunenthal Gmbh to the Counterclaims of Defendant Sandoz Inc. Purdue Pharma L.P., et al. v. Sandoz Inc., C.A. No. 1:11-cv-04694-UA (SDNY 2011).
Answer by Plaintiff/Counterclaim-Defendant Grunenthal Gmbh to the Counterclaims of Defendant Teva Pharmaceuticals, Inc., Purdue Pharma L.P., et al. v Teva Pharmaceuticals USA, Inc., C.A. No. 1:11-cv-02037-UA (SDNY 2011).
Answer of Plaintiff Purdue to the Counterclaims of Defendant Teva Pharmaceuticals USA, Inc., Purdue Pharma L.P., et al. v Teva Pharmaceuticals USA, Inc., C.A. No. 1:11-cv-02037-UA (SDNY 2011).
Answer of Plaintiff Purdue to the First Amended Counterclaims of Defendant Teva Pharmaceuticals USA, Inc., C.A. No. 1:11-cv-2037-SHS (SDNY 2011).
Answer of Plaintiff/Counterclaim-Defendant Grunenthal GMBH to the Counterclaims of Defendant Impax Laboratories, Inc., Purdue Pharma L.P., et al. v. Impax Laboratories Inc, C.A. No. 1:11-cv-02400-UA (SDNY 2011).
Answer of Plaintiffs Purdue and University of Texas System to the Counterclaims of Defendant Actavis Elizabeth LLC, Purdue Pharma L.P., et al. v. Actavis Elizabeth LLC, C.A. No. 1:11-cv-02038-UA (SDNY 2011).
Answer of Plaintiffs Purdue and University of Texas System to the Counterclaims of Defendant Impax Laboratories, Inc., Purdue Pharma L.P., et al. v. Impax Laboratories Inc, C.A. No. 1:11-cv-02400-UA (SDNY 2011).
Answer of Plaintiffs Purdue and University of Texas System to the Counterclaims of Defendant Sandoz Inc., Purdue Pharma L.P., et al. v. Sandoz Inc., C.A. No. 1:11-cv-04694-UA (SDNY 2011).
Answer, Affirmative Defenses, and Counterclaims of Defendant Impax Laboratories, Inc., Purdue Pharma L.P., et al. v. Impax Laboratories Inc, C.A. No. 1:11-cv-02400-UA (SDNY 2011).
Answer, Purdue Pharma L.P., et al. v. Watson Laboratories, Inc., et al., C.A No. 1:11-cv-02036-UA (SDNY 2011).
Arch. Pharm. Med. Chem. 1996, v. 329, pp. 325-326.
Arch. Pharm. Pharm. Med. Chem. vol. 329 (6), pp. 325-326, (1996).
Arch. Pharm. Pharm. Med. Chem. vol. 332 (10), pp. 369-370 (1999).
Australian Register of Therapeutic Goods entry for Codeine Linctus APF and Dymadon Forte (codeine phosphate; ARTG IDs: 14277 and 10956, respectively), produced Jun. 25, 2009.
Australian Register of Therapeutic Goods entry for Dilaudid (hyromorphone Hydrochloride, ARTG ID: 67353), produced Jun. 25, 2009.
Australian Register of Therapeutic Goods entry for Endone (oxycodone hydrochloride; ARTG ID: 14945), produced Jun. 25, 2009.
Australian Register of Therapeutic Goods entry for Ordine (morphine hydrochloride; ARTG IDs: 10780, 10779 and 10782), produced Jun. 25, 2009.
Auterhoff, et al., pp. 420-428 (1994).
B. Proksa, Separation of Products of Thebaine Rearrangement by Capillary Electrophoresis in the Presence of Cyclodextrins, 55 Chemical Papers 196 (2001).
Balanceanu, J. C. et al., Investigation of Rates and Mechanisms of Reactions ($2^{nd}$ ed) in 'Technique of Organic Chemistry: vol. 8, Part 1,' Interscience Publishers, Inc., pp. 11 (1961).
Bari et al., Impurity Profile: Significance in Active Pharmaceutical Ingridient, Eurasian Journal of Analytical Chemistry, vol. 2, No. 1, 2007.
Barton, D.H.R., The conformation of the Steroid Nucleus, Experientia, vol. VI/8:316-320 (1950).
Berge, Stephen, M., Pharmaceutical Salts, Journal of Pharmaceutical Sciences, 1977, v. 66, pp. 1-19.
Brief of Amici Curiae Donald E. Knebel and Mark D. Janis in Support of Appellants Purdue Pharma L.P., et al,; United States Court of Appeals for the Federal Circuit; Case 14-1294; Document 71; Filed Oct. 31, 2014.
Brief of Defendants—Appellees Mylan Pharmaceuticals Inc. and Mylan Inc.; United States Court of Appeals for the Federal Circuit; Case 14-1294; Document 130; Filed Apr. 1, 2015.
Brief of Plaintiffs—Appellants Purdue Pharma L.P., The P.F. Laboratories, Inc., Purdue Pharmaceuticals L.P., and Rhodes Technologies; United States Court of Appeals for the Federal Circuit; Case 14-1294; Document 52; Filed Oct. 6, 2014.
Buckett, W.R., "The relationship between analgesic activity, acute toxicity arid chemical structure in esters of 14-hydroxycodeinone," J. Pharm. Pharmacol, (1964), vol. 16, pp. 68T-71T.
Buckett, W.R., et al., "The analgesic properties of some 14-substituted derivatives of codeine and codeinone," J. Pharm. Pharmacol, (1964), vol. 16, pp. 174-182.

(56) References Cited

OTHER PUBLICATIONS

Carey et al., Advanced Organic Chemistry, pp. 1022-1105, 3rd ed. (1990).
Chapman v. Casner, (C.A. Fed. Aug. 25, 2008); Brief of Appellants.
Chapman v. Casner, (C.A. Fed. Dec. 4, 2008); Reply Brief of Cross-Appellants.
Chapman v. Casner, (C.A. Fed. Nov. 17, 2008); Response and Reply Brief of Appellants.
Chapman v. Casner, (C.A. Fed. Oct. 6, 2008); Brief of Cross-Appellants.
Chapman v. Casner, 2009 WL 606065 (C.A. Fed. Mar. 11, 2009) (opinion for the court filed by Circuit Judge Prost; dissenting opinion filed by Circuit Judge Rader).
Chemical and Pharmaceutical Bulletin 1962, v. 10, pp. 755-757.
Chemistry 1B Topic manual Flinders University, p. 114-5, 117 and 119 (2003).
Citizen Petition filed by Purdue Pharma L.P. and Rhodes Technologies on Oct. 10, 2007.
Citizen Petition on behalf of Endo Pharmaceuticals dated May 13, 2010.
Column Chromatography, Wikipedia, http://en.wikiedia.o•clvv;Inciex.h )7fifie`--` Colurnnchromatora )h .&rintaNe`--' es; retrieved on Mar. 13, 2013.
Complaint, Purdue Pharma L.P., et al. v Teva Pharmaceuticals USA, Inc., C.A. No. 1:11-cv-02037-UA (SDNY 2011).
Complaint, Purdue Pharma L.P., et al. v. Actavis Elizabeth LLC, C.A. No. 1:11-cv-02038-UA (SDNY 2011).
Complaint, Purdue Pharma L.P., et al. v. Amneal Pharmaceuticals, LLC., C.A. No. 11-cv-8153 (SDNY 2011).
Complaint, Purdue Pharma L.P., et al. v. Andrx Labs, LLC, C.A. No. 11 CIV 00248 (DDDE 2011).
Complaint, Purdue Pharma L.P., et al. v. Impax Laboratories Inc, C.A. No. 1:11-cv-02400-UA (SDNY 2011).
Complaint, Purdue Pharma L.P., et al. v. Ranbaxy Inc., et al., C.A. No. 10-03734-SHS (SDNY 2010).
Complaint, Purdue Pharma L.P., et al. v. Ranbaxy Inc., et al., C.A No. 1:11-cv-2401-UA (SDNY 2011).
Complaint, Purdue Pharma L.P., et al. v. Sandoz Inc., C.A. No. 1:11-cv-04694-UA (SDNY 2011).
Complaint, Purdue Pharma L.P., et al. v. Varam Inc., et al., C.A. No. 10-cv-04028-PBT (EDPA 2010).
Complaint, Purdue Pharma L.P., et al. v. Varam, Inc., et al., C.A. No. 10 CIV 6038 (SDNY 2010).
Complaint, Purdue Pharma L.P., et al. v. Watson Laboratories, Inc., et al., C.A No. 1:11-cv-02036-UA, (SDNY 2011).
Complaint, Purdue Pharma L.P., et al. v. Watson Laboratories, Inc., C.A. No. 0:11-cv-60643-xxxx (SDFL 2011).
Complaint, Purdue Pharma L.P., et al. v. Ranbaxy Inc., et al., C.A. No. 11-cv-7104 (SDNY 2011).
D. Swern et al., "Hydroxylation of Monounsatuated Fatty Materials VVith Hydrogen Peroxide," Journal of the American Chemical Society, 1945, vol. 67, No. 10, p. 1786.
D. Swern et al., "Hydroxylation of Monounsatuated Fatty Materials VVith Hydrogen Peroxide," Journal of the American Chemical Society, 1945, vol. 67, No. 10, p. 1786-1789.
Daniel C. Harris, Quantitative Chemical Analysis 646 (5th ed. 1999).
Day 1 Trial Transcript—Purdue Pharma LP, et al., v Actavis Elizabeth LLC, et al. Nov. 16, 2012.
Day 2 Trial Transcript—Purdue Pharma LP, et al., v Actavis Elizabeth LLC, et al. Nov. 19, 2012.
Day 3 Trial Transcript—Purdue Pharma LP, et al., v Actavis Elizabeth LLC, et al. Nov. 20, 2012.
Day 4 Trial Transcript—Purdue Pharma LP, et al. v Actavis Elizabeth LLC, et al. Nov. 21, 2012.
Day 5 Trial Transcript—Purdue Pharma LP, et al., v Actavis Elizabeth LLC, et al. Nov. 26, 2012.
Day 6 Trial Transcript—Purdue Pharma LP, et al. v Actavis Elizabeth LLC, et al. Nov. 27, 2012.
Day 7 Trial Transcript—Purdue Pharma LP, et al., v Actavis Elizabeth LLC, et al. Nov. 28, 2012.
Day 8 Trial Transcript—Purdue Pharma LP, et al., v Actavis Elizabeth LLC, et al. Dec. 12, 2012.
Decision revoking the European Patent issued in connection with European Application No. Application No. 05 730 345.5 on Nov. 8, 2013.
Declaration of Professor Gilbert Stork, Ph.D. of Aug. 1, 2007.
Declaration of Steven W. Baldwin, Ph.D. of Jul. 31, 2007.
Defendants Ranbaxy Inc.'s Answer and Counterclaims, Purdue Pharma L.P., et al. v. Ranbaxy Inc., et al., C.A. No. 10-03734-SHS (SDNY 2010).
Defendants Ranbaxy Inc.'s Answer and Counterclaims, Purdue Pharma L.P., et al. v. Ranbaxy Inc. et al., C.A. No. 1:11-cv-2401 (SDNY 2011).
Donovan, P. and Tweddell, E. The Faulding Formula—A History of F. H. Faulding & Co Limited, 1995, the Griffin Press, p. 129).
E.F. Fiese & S. H. Steffen, Comparison of the Acid Stability of Azithromycin and Erythromycin A, 25 J. Antimicrobial Chemotherapy 39 (Stipp. A 1990).
E.J. Lien, et al., "QSAR of narcotic analgetic agents," QSAR Research Monograph 22, pp. 186-196, G Barnet, M. Trsic, and R. Willette, eds. National Institute on Drug Abuse (1978).
Eder, Edwin et al., "Molecular Mechanisms of DNA Damage Initiated by a, 13—Unsaturated Carbonyl Compounds as Criteria for Genotoxicity and Mutagenicity," Environmental Health Perspectives, vol. 88, pp. 99-106 (1990).
English translation of Feldman et al., Obtaining of Dihydroxycodeinone Hydrochloride From Thebaine, Journal of Applied Chemistry, vol. XVIII, No. 11-12 (1945), including the article in russian.
English Translation of Japanese Office Action issued in connection with Japanese Patent Application No. 2007506507 dated Dec. 21, 2010.
English translation of notice of opposition filed against Costa Rican Divisional Application No. 20110376 dated Jan. 13, 2012.
English Translation of SU 64699 published on May 31, 1945.
English translation of the Office Action Issued by the Japanese Patent Office in connection with corresponding Japanese Patent Application No. 2011-251260 dated Jun. 12, 2012.
English translation of the Office Action Issued by the Korean Patent Office in connection with corresponding Korean Patent Application No. 10-2012-7006697 dated Jul. 5, 2012.
English translation of the Office Action Issued by the Korean Patent Office in connection with corresponding Korean Patent Application No. 10-2012-7017379 dated Aug. 13, 2012.
English translation of the Office Action issued in connection with corresponding Taiwanese application dated Aug. 20, 2014.
English translation of the opposition brief filed on behalf against European Patent No. 1 730 151 on Dec. 8, of Acino Pharma AG 2011.
English translation of the opposition brief filed on behalf of Asociacion de la Industria Farmaceuitca Nacional (ASIFAN) against Costa Rican Divisional Application No. 2011-0376 on Jan. 25, 2012.
English Translation of the Opposition to Costa Rican patent application No. 8593, filed by AssociaciOn de la Industria Farmaceutica National (ASIFAN) on Aug. 21, 2007.
English translation of Viebock, Chem. Ber. (1934), pp. 197-292.
European Search Report issued in connection with European Patent Application No. 10011792.8-2123 dated Jan. 31, 2011.
European Search Report dated Mar. 28, 2011 in connection with European Patent Application No. 10011788.6-2117.
Evidence in answer filed on Apr. 2, 2014 Easton declaration in connection with Australian Patent No. 2009200335.
Evidence in reply filed Sep. 2, 2014 Marshall declaration in connection with Australian Patent No. 2009200335.
Exhibit 1024 from US patent interference 105,553: Citizen Petition Filed on Oct. 10, 2007.
Exhibit 1027 From US patent Interference 105,553: transcript of the Videotaped Deposition of Steven W. Baldwin, Ph.D., taken on Sep. 21, 2007.
Exhibit E1 from the Opposition filed by Actavis Group on Dec. 9, 2011, against European patent 1 730 151.

(56) References Cited

OTHER PUBLICATIONS

Experimental aim/Experimental report, document A11, Oct. 28, 2015.
FDA Response issued on Nov. 21, 2011 to the Petition Submitted on Behalf of Lehigh Valley Technologies, Inc., and Glenmark Generics, Inc. dated May 31, 2011.
FDA Response to Citizen Petition and Petition for Stay of Action, Mar. 24, 2008.
Fleming, I. Selected Organic Syntheses: A Guidebook for Organic Chemists, John Wiley & Sons Ltd, pp. 506 and 80-84 (1973).
Frank Hollmann, "Coupling Homogeneous and Enzyme Catalysis for Highly Specific Hydroxylation, Epoxidations and Hydrogenations," a dissertation submitted to the Swiss Federal Institute of Technology Zurich, (2003), Nr. 15369 (2004), including NEBIS data.
Freund and Speyer, J. Prakt. Chem. 135-178 (1916).
Freund und Speyer, pp. 135-178 (1917).
G. Marc Loudon & Joseph G Stowell, "*Dehydration of B-Hydroxyl Carbonyl Compounds*", Study Guide and Solutions Manual to Accompany Organic Chemistry, Fourth Edition, Oxford University Press, New York, 2003, pp. 813-814.
G. Marc Loudon, *Organic Chemistry, Fourth Edition*, Oxford University Press, New York, 2002, pp. 150151 (Section 4.9A), 291-292 (Section 7.9E), 408-411 (Section 10.1), 1016-1017 (Section 22.4B) and 10521053 (Section 22.9), 2002.
G. Stork & J. Puls, "*Biochemistry and Molecular Genetics of Clostridium Thermocellum Cellulases—Comparative Characterisation of Cellulose Hydrolysis,*" *Cellulose Hydrolysis and Fermentation*, J. Coombs & G. Grassi, Eds., CPL Press, 1992.
G. Toennies & R.P. Homiller, "*The Oxidation of Amino Acids by Hydrogen Peroxide in Formic Acid*", Journal of the American Chemical Society, 1942, vol. 64, No. 12, pp. 3054-3056.
Gould, M. E. *Chemistry Laboratory Manual: A Scientific Process Approach* McGraw-Hill Book Company, pp. 2-4 (1996).
Gould, M. E. Chemistry Laboratory Manual: A Scientific Process Approach, McGraw-Hill Book Company, pp. 5-7 (1996).
Grigg, E. C. M. and Plowman, R. A. Practical Chemistry I: Notes for Agriculture, Engineering, Forestry, Pharmacy, Physiotherapy, Science, Surveying ($2^{nd}$ Ed) University of Queensland Press, pp. 55-57 (1966).
Grigg, E. C. M. and Plownman, R. A., Practical Chemistry I: Notes for Agriculture, Engineering, Forestry, Pharmacy, Physiotherapy, Science Surveying ($2^{nd}$ ed.) University of Queensland Press, pp. 58-60 (1966).
Grigor'eva, The Stereochemistry and Mechanism of Dehydration of Cyclohexane Derivatives, Russ. Chem. Rev., 31(1): 18-35 (1962).
Gyongyi Gulyas et al., Morphine Alkaloids, 104: Synthesis and Conversions of New Epoxy Derivatives, 125 Acta Chimica Hungarica 255 (1988).
H. Schmidhammer, et al., "Synthesis and biological evaluation of 14-alkoxymorphinans," Helvetica Chimica Acta vol. 72, pp. 1233-1240 (1989).
H. Schmidhammer, et al., "Synthesis and biological evaluation of 14-alkoxymorphinans: Extensive study on cyprodime-related compounds," J. Medicinal Chemistry vol. 33, pp. 1200-1206 (1990).
H. Tada et al. "Ketalisation of ap-unsaturated ketones. Part I: 3-methoxy-N-methylmorphinan derivatives and 14-hydroxycodeine-one" Tetrahedron Letters No. 22, pp. 1805-1808 (1969).
Hauser et al., "14-Hydroxycodeinone. An Improved Synthesis", Journal of Medicinal Chemistry, 1974, vol. 17, No. 10, p. 1117.
Henschler et al., *Structure Activity Relationships of a, B-Unsaturated Carbonylic Compounds*, IARC Sci Publ., vol. 70, 1986, pp. 197-205.
Hudlicky, M. Reductions in Organic Chemistry, John Wiley & Sons (1984).
Ikuo Iijima et al., *The Oxidation of Thebaine with m-Chloroperbenzoic Acid Studies in the (+)—Morphinan Series*. III, 60 Helvetica Chimica Acta, 2135-2137, 1977.
Interference No. 105,553, Annotated Claims, May 17, 2007.
Interference No. 105,553, CAFC Decision, Mar. 11, 2009.
Interference No. 105,553, Casner Certificate of Filing of the Record, Jan. 31, 2008.
Interference No. 105,553, Casner Clean Claims, May 3, 2007.
Interference No. 105,553, Casner Exhibit List as of Aug. 2, 2007, Aug. 2, 2007.
Interference No. 105,553, Casner Identification of Counsel, May 3, 2007.
Interference No. 105,553, Casner Identification of Real Party in Interest, May 3, 2007.
Interference No. 105,553, Casner Identification of Related Proceedings, May 3, 2007.
Interference No. 105,553, Casner List of Proposed Motions, May 25, 2007.
Interference No. 105,553, Casner Motion 1 (Judgment for No Interference-in-Fact), Aug. 2, 2007.
Interference No. 105,553, Casner Motion 8 (Judgment for Indefiniteness), Aug. 2, 2007.
Interference No. 105,553, Casner Motions 2-5 (Motion to Deny Chapman the Benefit of Earlier-Filed Application), Aug. 2, 2007.
Interference No. 105,553, Casner Motions 6-7 (Judgment for Lack of Written Description and Enablement), Aug. 2, 2007.
Interference No. 105,553, Casner Motions 9-10, Judgment based on 35 U.S.C. 103), Aug. 2, 2007.
Interference No. 105,553, Casner Notice of Judicial Review, May 27, 2008.
Interference No. 105,553, Casner Power of Attorney, May 3, 2007.
Interference No. 105,553, Chapman Clean Involved Claims, May 3, 2007.
Interference No. 105,553, Chapman Exhibit List (Exhibits in Chapman's Substantive Motions), Aug. 2, 2007.
Interference No. 105,553, Chapman Exhibit List (Master List of Chapman Record Exhibits), Jan. 31, 2008.
Interference No. 105,553, Chapman List of Proposed Motions, May 25, 2007.
Interference No. 105,553, Chapman Miscellaneous Reply 1 (Reply to Casner 2008 Opposition to Chapman Motion to Exclude), Jan. 24, 2008.
Interference No. 105,553, Chapman Notice of Appeal, May 12, 2008.
Interference No. 105,553, Chapman Notice of change of Address of Counsel, May 25, 2007.
Interference No. 105,553, Chapman Notice of filing Priority Statement, Aug. 2, 2007.
Interference No. 105,553, Chapman Notice of Lead and Backup Counsel, May 3, 2007.
Interference No. 105,553, Chapman Notice of Real Party-in-Interest, May 3, 2007.
Interference No. 105,553, Chapman Notice or Related Proceedings, May 3, 2007.
Interference No. 105,553, Chapman request for File, May 3, 2007.
Interference No. 105,553, Chapman Submission of Substantive Motions Record (Time Period 8: Submission of Record for Decision on Motions) Jan. 31, 2008.
Interference No. 105,553, Chapman Substantive Motions 1-2 (For Benefit of Application Nos. 60651778), Aug. 2, 2007.
Interference No. 105,553, Corrected Priority Statement, Aug. 14, 2007.
Interference No. 105,553, Declaration, Apr. 19, 2007.
Interference No. 105,553, Exhibit 1001, Jan. 31, 2008.
Interference No. 105,553, Exhibit 1002, Jan. 31, 2008.
Interference No. 105,553, Exhibit 1003, Jan. 31, 2008.
Interference No. 105,553, Exhibit 1004, Jan. 31, 2008.
Interference No. 105,553, Exhibit 1005, Jan. 31, 2008.
Interference No. 105,553, Exhibit 1006, Jan. 31, 2008.
Interference No. 105,553, Exhibit 1007, Jan. 31, 2008.
Interference No. 105,553, Exhibit 1008, Jan. 31, 2008.
Interference No. 105,553, Exhibit 1009, Jan. 31, 2008.
Interference No. 105,553, Exhibit 1010, Jan. 31, 2008.
Interference No. 105,553, Exhibit 1011, Jan. 31, 2008.
Interference No. 105,553, Exhibit 1012, Jan. 31, 2008.
Interference No. 105,553, Exhibit 1013, Jan. 31, 2008.
Interference No. 105,553, Exhibit 1014, Jan. 31, 2008.
Interference No. 105,553, Exhibit 1015, Jan. 31, 2008.

(56) References Cited

OTHER PUBLICATIONS

Interference No. 105,553, Exhibit 1016, Jan. 31, 2008.
Interference No. 105,553, Exhibit 1017, Jan. 31, 2008.
Interference No. 105,553, Exhibit 1018, Jan. 31, 2008.
Interference No. 105,553, Exhibit 1019, Jan. 31, 2008.
Interference No. 105,553, Exhibit 1020, Jan. 31, 2008.
Interference No. 105,553, Exhibit 1021, Jan. 31, 2008.
Interference No. 105,553, Exhibit 1022, Jan. 31, 2008.
Interference No. 105,553, Exhibit 1023, Jan. 31, 2008.
Interference No. 105,553, Exhibit 1024, Jan. 31, 2008.
Interference No. 105,553, Exhibit 1025, Jan. 31, 2008.
Interference No. 105,553, Exhibit 1026, Jan. 31, 2008.
Interference No. 105,553, Exhibit 1027, Jan. 31, 2008.
Interference No. 105,553, Exhibit 1028, Jan. 31, 2008.
Interference No. 105,553, Exhibit 1029, Jan. 31, 2008.
Interference No. 105,553, Exhibit 1030, Jan. 31, 2008.
Interference No. 105,553, Exhibit 1031, Jan. 31, 2008.
Interference No. 105,553, Exhibit 1032, Jan. 31, 2008.
Interference No. 105,553, Exhibit 1033, Jan. 31, 2008.
Interference No. 105,553, Exhibit 1034, Jan. 31, 2008.
Interference No. 105,553, Exhibit 1035, Jan. 31, 2008.
Interference No. 105,553, Exhibit 1036, Jan. 31, 2008.
Interference No. 105,553, Exhibit 1037, Jan. 31, 2008.
Interference No. 105,553, Exhibit 1038, Jan. 31, 2008.
Interference No. 105,553, Exhibit 1039, Jan. 31, 2008.
Interference No. 105,553, Exhibit 1040, Jan. 31, 2008.
Interference No. 105,553, Exhibit 1041, Jan. 31, 2008.
Interference No. 105,553, Exhibit 1042, Jan. 31, 2008.
Interference No. 105,553, Exhibit 2001, Jan. 31, 2008.
Interference No. 105,553, Exhibit 2002, Jan. 31, 2008.
Interference No. 105,553, Exhibit 2003, Jan. 31, 2008.
Interference No. 105,553, Exhibit 2004, Jan. 31, 2008.
Interference No. 105,553, Exhibit 2005, Jan. 31, 2008.
Interference No. 105,553, Exhibit 2006, Jan. 31, 2008.
Interference No. 105,553, Exhibit 2007, Jan. 31, 2008.
Interference No. 105,553, Exhibit 2008, Jan. 31, 2008.
Interference No. 105,553, Exhibit 2009, Jan. 31, 2008.
Interference No. 105,553, Exhibit 2010, Jan. 31, 2008.
Interference No. 105,553, Exhibit 2011, Jan. 31, 2008.
Interference No. 105,553, Exhibit 2012, Jan. 31, 2008.
Interference No. 105,553, Exhibit 2013, Jan. 31, 2008.
Interference No. 105,553, Exhibit 2014, Jan. 31, 2008.
Interference No. 105,553, Exhibit 2015, Jan. 31, 2008.
Interference No. 105,553, Exhibit 2016, Jan. 31, 2008.
Interference No. 105,553, Exhibit 2017, Jan. 31, 2008.
Interference No. 105,553, Exhibit 2018, Jan. 31, 2008.
Interference No. 105,553, Exhibit 2019, Jan. 31, 2008.
Interference No. 105,553, Exhibit 2020, Jan. 31, 2008.
Interference No. 105,553, Exhibit 2021, Jan. 31, 2008.
Interference No. 105,553, Exhibit 2022, Jan. 31, 2008.
Interference No. 105,553, Exhibit 2023, Jan. 31, 2008.
Interference No. 105,553, Exhibit 2024, Jan. 31, 2008.
Interference No. 105,553, Exhibit 2025, Jan. 31, 2008.
Interference No. 105,553, Exhibit 2026, Jan. 31, 2008.
Interference No. 105,553, Exhibit 2027, Jan. 31, 2008.
Interference No. 105,553, Exhibit 2028, Jan. 31, 2008.
Interference No. 105,553, Exhibit 2029, Jan. 31, 2008.
Interference No. 105,553, Exhibit 2030, Jan. 31, 2008.
Interference No. 105,553, Exhibit 2032, Jan. 31, 2008.
Interference No. 105,553, Exhibit 2033, Jan. 31, 2008.
Interference No. 105,553, Exhibit 2034, Jan. 31, 2008.
Interference No. 105,553, Exhibit 2035, Jan. 31, 2008.
Interference No. 105,553, Exhibit 2036, Jan. 31, 2008.
Interference No. 105,553, Exhibit 2037, Jan. 31, 2008.
Interference No. 105,553, Exhibit 2038, Jan. 31, 2008.
Interference No. 105,553, Exhibit 2039, Jan. 31, 2008.
Interference No. 105,553, Exhibit 2040, Jan. 31, 2008.
Interference No. 105,553, Exhibit 2041, Jan. 31, 2008.
Interference No. 105,553, Exhibit 2042, Jan. 31, 2008.
Interference No. 105,553, Exhibit List as of Dec. 20, 2007.
Interference No. 105,553, Exhibit List as of Jan. 10, 2008, Jan. 10, 2008.
Interference No. 105,553, Exhibit List as of Nov. 19, 2007, Nov. 19, 2007.
Interference No. 105,553, Exhibit List as of Oct. 10, 2007, Oct. 10, 2007.
Interference No. 105,553, Exhibit List, Dec. 10, 2007.
Interference No. 105,553, Exhibit List, Dec. 20, 2007.
Interference No. 105,553, Exhibit List, Nov. 19, 2007.
Interference No. 105,553, Exhibit List, Oct. 10, 2007.
Interference No. 105,553, Joint Statement Regarding Settlement Negotiations, Jul. 18, 2007.
Interference No. 105,553, Joint Stipulation to Change Time Periods 4, Nov. 8, 2007.
Interference No. 105,553, Joint Stipulation to Change Time Period 3, Sep. 21, 2007.
Interference No. 105,553, Judgment, Mar. 13, 2008.
Interference No. 105,553, Memo to Parties—Re: Conference Call Not Required, Jul. 18, 2007.
Interference No. 105,553, Miscellaneous Motion 1, Dec. 20, 2007.
Interference No. 105,553, Notice of Serving Priority Statement, Aug. 9, 2007.
Interference No. 105,553, Observations, Dec. 20, 2007.
Interference No. 105,553, Opposition 1, Jan. 10, 2008.
Interference No. 105,553, Opposition 1, Oct. 10, 2007.
Interference No. 105,553, Opposition 1-2, Oct. 10, 2007.
Interference No. 105,553, Opposition 2-5, Oct. 10, 2007.
Interference No. 105,553, Opposition 6-7, Oct. 10, 2007.
Interference No. 105,553, Opposition 8, Oct. 10, 2007.
Interference No. 105,553, Opposition 9-10, Oct. 10, 2007.
Interference No. 105,553, Order Accepting Corrected Priority Statement, Aug. 16, 2007.
Interference No. 105,553, Order—Bd.R. 109(b) Authorizing of Office Records, May 8, 2007.
Interference No. 105,553, Order Canceling Oral Argument, Feb. 6, 2008.
Interference No. 105,553, Order Setting Oral Argument Date, Jan. 14, 2008.
Interference No. 105,553, Order-Motion Times-Bd.R. 104(c), Jun. 7, 2007.
Interference No. 105,553, Replies 1-2, Dec. 10, 2007.
Interference No. 105,553, Replies 1-2, Nov. 19, 2007.
Interference No. 105,553, Reply 1, Nov. 19, 2007.
Interference No. 105,553, Reply 2-5, Nov. 19, 2007.
Interference No. 105,553, Reply 6-7, Nov. 19, 2007.
Interference No. 105,553, Reply 8, Nov. 10, 2007.
Interference No. 105,553, Reply 9-10, Nov. 19, 2007.
Interference No. 105,553, Request for Oral Argument on Chapman Miscellaneous Motion 1, Dec. 28, 2007.
Interference No. 105,553, Request for Oral Argument, Dec. 20, 2007.
Interference No. 105,553, Response to Canner Observations, Jan. 10, 2008.
Interference No. 105,553, Second Joint Stipulation to Change Time Periods, Oct. 1, 2007.
Interference No. 105,553, Standing Order, Apr. 19, 2007.
Interference No. 105,553, Submission of License for Foreign Filing, Jun. 1, 2007.
Isao Seki, Improvement in Preparation of 14-Hydroxycodeinone, 12 Takamine Kenkusho Nempo 52 (1960).
Isao Seki, Studies on the Morphine Alkaloids and Its Related Compounds. XV: Isolations of 8 p,14 p-Epoxy-codide and 14-Hydroxy-dihydropsuedo-codeine from Some Nucleophilic Substitution Reaction Products of Tosylate of 14-Hydroxy-codeine or its Isomers, 17 Chemical & Pharm. Bull. 1549 (1969).
J. Pharm. Sci. (1979), pp. 43-45.
John McMurry, Organic Chemistry, pp. 249-252, $5^{th}$ ed. (2002).
Journal of Organic Chemistry 1958 v.23 pp. 1247-1251.
Kirchner, J. G., Thin-Layer Chromatography ($2^{nd}$ ed) in 'Techniques of Chemistry: vol. 14,' John Wiley & Sons, pp. 335-347 and 399-402 (1978).

(56) References Cited

OTHER PUBLICATIONS

Kirchner, J. G., Thin-Layer Chromatography ($2^{nd}$ Ed) in 'Techniques of Chemistry: vol. 14,' John Wiley & Sons, pp. 174-176 (1978).
Kotz, J. C. and Treichel, Jr., P., Chemistry & Chemical Reactivity ($4^{th}$ ed) Saunders College Publishing and Harcourt Brace College Publishers pp. 692-724 (1999).
Kragnig, R., et al., "Optimization of the synthesis of oxycodone and 5-methyloxycodone," *Arch. Pharm. Pharm. Med. Chem.*, (1996), pp. 325-326.
Krasnig et al., "Optimization of the Synthesis of Oxycodone and 5-Methyloxycodone", Arch. Pharm. Med. Chem., v, 329, pp. 325-326, 1996.
Krassnig et al., Arch. Pharm. Pharm. Med. Chem. (1996), pp. 325-326.
KW Bentley, The Chemistry of the Morphine Alkaloids, chapter XVIII, Oxford at the Clarendon Press, (1954).
KW Bentley, The Chemistry of the Morphine Alkaloids, chapter XVII, pp. 243-250, Oxford at the Clarendon Press (1954).
Letter from FDA to Purdue Pharma L.P., dated Jan. 2, 2004.
Letter from FDA to Rhodes Technologies, dated Jan. 6, 2004.
Letter from Purdue Pharma L.P. to FDA, dated Nov. 12, 2004.
Letter of Jan. 2, 2004 from U.S. Department of Health and Human Services to James 0. Kelly, Director, Regulatory Affairs, CMC, Purdue Pharma L.P.
Letter of Jan. 6, 2004 from U.S. Department of Health and Human Services to Tobert Loewenstein, Director, Regulatory Affairs, Rhodes Technologies.
LF Small, RE Lutz, Chemistry of the Opium Alkaloids, Suppl. No. 103 to Public Health Reports, pp. 250 to 260, Washington (1932).
lijima et al., J. Med. Chem. (1978), p. 398-400.
lijima, Ikuo et al., "Studies in the (+)-Morphine Series. Synthesis and Biological Properties of (+)-Naloxone," *Journal of Medicinal Chemistry*, vol. 21, No. 4, pp. 398-400 (1978).
Lippincott, W. T., Meek, D. W., Gailey, K. D., Whitten, K. W. Experimental General Chemistry, CBS College Publishing, pp. 425-431 (1984).
Lippincott, W. T., Meek, D. W., Gailey, K. D., Whitten, K. W., Experimental General Chemistry, CBS College Publishing, pp. 295-298 (1984).
Lopez et al., "The [4+2] Addition of Singlet Oxygen to Thebaine: New Access to Highly Functionalized Morphine Derivatives via Opioid Endoperoxides", Journal of Organic Chemistry 2000, 65, 4671-4678.
Lutz et al. "Reduction Studies in the Morphine Series. IX Hydroxycodeinone", *J.Org.* Chem., pp. 220-233 (1939).
Lutz et al., J. Org. Chem. (1939), pp. 220-233.
Lutz, Robert E. et al., "Reduction Studies in the Morphine Series. IX. Hydroxycodeinone," *The Journal of Organic Chemistry*, vol. 04, No. 3, pp. 110-133 (1939).
M. G. Vavon & Mile Boleslawa Jakubowicz, Contribution a l 'etude des cholestanols (a), 53 Bulletin Societe Chimique France 581 (1933).
M.U. Valhari et al. "Synthesis of 6-Methoxymethylmorphinol," Journal of the Chemical Society of Pakistan, vol. 13, pp. 169-173 (1991).
Matthews, J. C. A Modern Chemistry Laboratory Manual: A Scientific Process Approach, McGraw-Hill Book Company (1964).
Matthews, J. C. A Modern Day Chemistry Course, Hutchinson Educational, p. 18-19 (1964).
*McGraw Hill Dictionary of Scientific and Technical Terms*, p. 1061, $6^{th}$ ed 2003.
Memorandum of Law in Support of Plaintiffs' Rule 12(b)(6) Motion to Dismiss Actavis's Third Counterclaim, *Purdue Pharma L.P., et al. v. Actavis Elizabeth LLC*, C.A. No. 1:11-cv-02038-UA (SDNY 2011).
Memorandum Opinion and Order from US Patent Interference 105,553, Mar. 13, 2008.
Merck Index $13^{th}$ edition, p. 7028 (2001).
*Merck Index*, p. 6961, $14^{th}$ ed. 2006.

Michael B. Smith & Jerry March, March's Advanced Organic Chemistry: Reactions, Mechanisms, and Structure 1048 (5th ed. 2001).
Michael Dawson et at, A Rapid and Sensitive High-Performance Liquid Chromatography-Electro spray Ionization-Triple Quadrupole Mass Spectrometry Method for the Quantitation of Oxycodone in Human Plasma, 40 J. Chromatographic Science 40 (2002).
Mylan Pharmaceuticals Inc.'s and Mylan Inc.'s Answer and Counterclaims, *Purdue Pharma L.P., et al.* v. *Ranbaxy Inc., et al.*, C.A. No. 10-03734-SHS (SDNY 2010).
Nagamatsu K. et al., "In vitro formulation of codeinone from codeine by rat or guinea pig liver homogenate and its acute toxicity in mice," *Biochem Pharmacol.*, vol. 34, No. 17, pp. 3143-3146 (1985).
Nimitz, J. S., Experiments in Organic Chemistry: From Microscale to Macroscale, Prentice-Hall, Inc., pp. 2223 (1991).
Nimitz, L. S., Experiments in Organic Chemistry: From Microscale to Macroscale, Prentice-Hall, Inc., pp. 2233 and 34-44 (1991).
Notice of Certifications Letter on Behalf Notice of Paragraph IV Certification regarding NDA 02-0553 dated Mar. 23, 2010, re U.S. Pat. Nos. 7,674,799 and 7,674,800.
Notice of Certifications Letter on Behalf of Amendment to ANDA No. 200692 dated Apr. 9, 2010 re U.S. Pat. Nos. 7,674,799, and 7,674,800.
Notice of Certifications Letter on Behalf of Amendment to ANDA No. 200692 Paragraph IV Patent Certification dated Apr. 9, 2010 re U.S. Pat. Nos. 7,674,799, 7,674,800, and 7,683,072.
Notice of Certifications Letter on Behalf of ANDA 202762 dated May 23, 2011 re U.S. Pat. Nos. 6,488,963, 7,674,799, 7,674,800, and 7,776,314.
Notice of Certifications Letter on Behalf of ANDA No. 200692 Paragraph Patent IV Patent Certification dated Apr. 1, 2010, re U.S. Pat. Nos. 7,674,799, and 7,674,800.
Notice of Certifications Letter on Behalf of Invalidity and or Non Infringement dated Feb. 7, 2011, re U.S. Pat. Nos. 6,488,963, 7,674,799, 7,683,072, 7,776,314.
Notice of Certifications Letter on Behalf of Invalidity and or Non Infringement dated Feb. 7, 2011 re U.S. Pat. Nos. 6,488,963, 7,674,799, 7,674,800, 7,683,072, and 7,776,314.
Notice of Certifications Letter on Behalf of Notice of ANDA No. 202455 with Paragraph IV certification dated Feb. 9, 2011 re U.S. Pat. Nos. 7,674,799, 7,674,800, 7,683,072 and 7,776,314.
Notice of Certifications Letter on Behalf of Notice of Paragraph Certification of Invalidity and No Infringement dated Jun. 28, 2010, re U.S. Pat. Nos. 5,508,042, 7,674,799, 7,674,800, and 7,683,072.
Notice of Certifications Letter on Behalf of Notice of Paragraph IV Certification Regarding NDA 02-2272 dated Feb. 24, 2011 re U.S. Pat. Nos. 6,488,963, 7,674,799, 7,674,800, 7,683,072, and 7,776,314.
Notice of Certifications Letter on Behalf of Notice of Paragraph IV Certification Regarding NDA 02-0553 dated Apr. 8, 2010 re U.S. Pat. No. 7,683,072.
Notice of Certifications Letter on Behalf of Notice Pursuant to 505(j)(2)(B)(ii) of the Federal Drug , and Cosmetic Act dated Feb. 15, 2011 re U.S. Pat. Nos. 7,674,799 , 7,674,800, 7,683,072 , 6,488,963, and 7,776,314.
Notice of Certifications Letter on Behalf of Notification to 505(j)(2)(B)(ii) of the Federal Drug, and Cosmetic Act dated Apr. 8, 2010 re U.S. Pat. Nos. 7,674,799, 7,674,800, and 7,683,072.
Notice of Certifications Letter on Behalf of Paragraph IV Patent Certification Notice dated Feb. 23, 2011 re U.S. Pat. Nos. 6,488,963, 7,674,799, 7,683,072, 7,776,314.
Notice of Final Rejection dated May 13, 2013, in connection with Korean Patent Application No. 102012-7006697.
Notice of Opposition filed on Feb. 6, 2009, in Australian patent application No. 2005230826.
O'Connor, P. R. Davis, Jr., J. E., Haenisch, E. L., MacNab, W. K., McClellan, A. L., Chemistry: Experiments and Principles, D. C. Heath and Company, pp. 243-246, 250-254, 258 (1977).
O'Connor, P.R., Davis, Jr., J. E., Haenisch, E. L., MacNab, W. K., McClellan, A. L., Chemistry: Experiments and Principles, D. C. Heath and Company, pp. 369-370 (1977).
Office Action dated Apr. 11, 2013, in connection with Vietnamese Patent Application No. 1-201101628.

(56) References Cited

OTHER PUBLICATIONS

Office Action dated Oct. 23, 2012, in connection with Japanese Patent Application No. 2011251260.
Opponent 2's Submission filed on Jul. 19, 2013, in corresponding European Patent No. 1 730 151.
Opponent 1's Submission filed on Jul. 19, 2013, in corresponding European Patent No. 1 730 151.
Opposition brief filed on behalf of Actavis Group against European Patent No. 1 730 151 on Dec. 9, 2011.
Opposition brief filed on behalf of Almut Susanne Elend against European Patent No. 1 730 151 on Dec. 5, 2011.
Organic Chemistry 2 Laboratory Manual Flinders University, pp. 7, 9, 10, and 13 to 37 (2002).
Organic Chemistry 3 Laboratory Manual Flinders University, pp. 5-12 (2002).
Pasto, et al. "Organic Reactions," vol. 40, p. 91-155, (1991).
Patent Examination Report No. 1, dated Jan. 31, 2013, in connection with Australian Patent Application No. 2011213801.
Patentee's Reply to the Summons to Oral Proceedings filed on Jul. 19, 2013, in corresponding European Patent No. 1 730 151.
Patentee's response to (i) the opposition brief filed on behalf of Actavis Group against European Patent No. 1 730 151 on Dec. 9, 2011, (ii) the opposition brief filed on behalf of Acino Pharma AG against European Patent No. 1 730 151 on Dec. 8, 2011, and (iii) the opposition brief filed on behalf of Almut Susanne Elend against European Patent No. 1 730 151 on Dec. 5, 2011, the response dated Jul. 27, 2012.
PBS and ARTG entries for Kapanol (morphine sulphate; PBS code 2841M; ARTG IDs: 48136, 48134 and 48135) and MS Contin (morphine sulphate; PBS code: 1653BARTG ID: 14461), produced Jun. 25, 2009.
PBS and ARTG entries for OxyContin (oxycodone hydrochloride; PBS codes; 8385H, 8386J, 8387K, 8388L; ARTG IDs; 68187, 68188, 68190, 68189, 68191, 68192, 68193 and 68194, respectively, produced Jun. 25, 2009.
Perry E. S. and Weissberger, A. Separation and Purification ($3^{rd}$ ed) in 'Technques of Chemistry: vol. 12', John Wiley & Sons, pp. 67-68 (1978).
Perry, E. S. and Weissberger, A. Separation and Purification ($3^{rd}$ Ed.) in 'Techniques of chemistry: vol. 12,' John Wiley & Sons, pp. 240-246 and 349-351 (1978).
Perry E. S. and Weissberger, A., Separation and Purification ($3^{rd}$ ed) in 'Techniques of Chemistry: vol. 12,' John Wiley & Sons, pp. 7-14 (1978).
Peter J. Maurer & Hemy Rapoport, Nitrogen-Bridged Conformationally Constrained Etorphine Analogues. Synthesis and Biological Evaluation, 30 J. Medicinal Chemistry 2016 (1987).
Petition for Reconsideration, Mar. 31, 2008.
Petition for Stay of Action filed by Purdue Pharma L.P. and Rhodes Technologies on Oct. 10, 2007.
Physician's Desk Reference, p. 2163, 51st ed. (1997).
Pierre Deslongchamps, Stereoelectronic Effects in Organic Chemistry 163 (1983).
Plaintiff Purdue's Notice of Motion and Rule 12(b)(6) Motion to Dismiss Actavis's Third Counterclaim, *Purdue Pharma L.P., et al. v. Actavis Elizabeth LLC*, C.A. No. 1:11-cv-02038-UA (SDNY 2011).
Plaintiffs' Answer to the Counterclaims of Defendant *Actavis Elizabeth LLC, Purdue Pharma L.P., et al. v. Ranbaxy Inc., et al.*, C.A. No. 10-03734-SHS (SDNY 2010).
Plaintiffs' Answer to the Counterclaims of Defendants *Mylan Pharmaceuticals Inc. and Mylan inc., Purdue Pharma L.P., et al. v. Ranbaxy Inc., et al.*, C.A. No. 10-03734-SHS (SDNY 2010).
Plaintiffs' Answer to the Counterclaims of Defendants *Ranbaxy Inc. et al., Purdue Pharma L.P et al. v. Ranbaxy Inc. et al.*, C.A. No. 1-10-cv-03734-SHS (SDNY 2010).
Plaintiffs' Answer to the Counterclaims of Defendants *Ranbaxy Inc. et al., Purdue Pharma L.P., et al. v. Ranbaxy Inc. et al.*, C.A. No. 1:11-cv-02401 (SDNY 2011).

Plaintiffs Answer to the Counterclaims of Defendants Ranbaxy Inc., Ranbaxy Pharmaceuticals, Inc. and Ranbaxy Laboratories Ltd., C.A. No. 1:11-cv-7104-SHS (SDNY 2011).
Plaintiffs' Corrected Reply in Support of Plaintiffs Rule 12(b) (6) Motion to Dismiss Actavis's Third Counterclaim, *Purdue Pharma L.P., et al. v. Actavis Elizabeth LLC*, C.A. No. 1:11-cv-02038-UA (SDNY 2011).
Plaintiffs Reply in Support of Plaintiffs Rule 12(b)(6) Motion to Dismiss Actavis's Third Claim, *Purdue Pharma L.P., et al v. Actavis Elizabeth LLC*, C.A. No. 1:11-cv-02038-UA (SDNY 2011).
Planner and Furst, Helv. Chim. Acta vol. 32, p. 275. (1949).
PNAS 1983, v. 80, pp. 5176-5180.
Prestera, Tory et al., "The Electrophile Counterattack Response: Protection Against Neoplasia and Toxicity," *Advan. Enzyme Regul.*, vol. 33, pp. 281-296 (1993).
Principal Brief of Appellee Amneal Pharmaceuticals, LLC; United States Court of Appeals for the Federal Circuit; Case 14-1294; Document 125; Filed Mar. 30, 2015.
Principal Brief of Appellee Teva Pharmaceutical USA, Inc,; United States Court of Appeals for the Federal Circuit; Case 14-1294; Document 128; Filed Apr. 1, 2015.
Principles in preparative HPLC; Agilent Technologies, Mar. 2004.
Proksa, Acrch. Pharm. Pharm. Med. Chem. (1999), pp. 369-370.
Public Health Service, "FR Daily: National Toxicology Program; Announcement of Intent to Conduct Toxicologial Studies of 16 Chemicals," *Alpha beta unsat ketones*, pp. 13-19 (1995).
*Purdue v. Teva*, Decision on Appeals from the United States District Court for the Southern District of New York in Nos. 1:11-cv-02037-SHS, 1:12-cv-05083-SHS, Case 14-1294 (# 173-1 Feb. 1, 2016).
*Purdue v. Teva*, Trial Decision (Case 04-MD-01603-SHS 568) (# 149 Jan. 14, 2014).
Purdue's Answer to the Counterclaims of Defendant *Varam, Inc., Purdue Pharma L.P., et. al. v. Varam Inc., et al.*, C.A. No. 10-cv-04028-PBT (EDPA 2010).
Ramanathan et al., Indian J Technol, pp. 350-351 (1964).
Ranbaxy's Notice of Paragraph IV Certification Regarding NDA 02-2272 dated Aug. 25, 2011.
Remington: The Science and Practice of Pharmacy, 382 (Alfonso R. Gennaro ed., $19^{th}$ ed. 1995).
Renzi Jr N L et al: "Quantitative GLC determination of oxycodone in human plasma" Journal of Pharmaceutical Sciences 1979 United States, vol. 68, No. 1, 1979, pp. 43-45, XP002428746.
Replaced Written Opinion dated Oct. 22, 2010, in connection with Singaporean Application No. 2006052575.
Robert Thornton Morrison & Robert Neilson Boyd, Organic Chemistry, 4th ed., pp. 325-393, 455-484 and 533-554 (1983).
Rylander, P. N. Catalytic Hydrogenation in Organic Synthesis, Academic Press, pp. 6-8, 31-36, 51-58. (1979).
Sandoz Inc.'s Answer, Affirmative Defenses and Counterclaims, *Purdue Pharma L.P., et al. v. Sandoz Inc.*, C.A. No. 1:11-cv-04694-UA (SDNY 2011).
Sargent et al., "Hydroxylated Codeine Derivatives," received Mar. 24, 1958.
Schatz, J., et al., "Synthesis and biological evaluation of 14-alkoxymorphinans. 20. 14 phenylpropxymetopon: an extremely powerful analgesic," *J. Med. Chem.*, (2003), vol. 46, pp. 4182-4187.
Schmidhammer, H., et al., "Synthesis and biological evaluation of 14-alkoxymmorphinans 14-methoxymetopon, an extremely potent opioid agonist," *Helvetica Chimica Acta*, vol. 73, (1990), pp. 1784-1787.
Schmidhammer, H., et al., "Synthesis, structure elucidation, and pharmacological evaluation of 5-methyl-oxymorphone," *Helvetica Chimica Acta*, vol. 71, (1988), pp. 1801-1804.
SciFinder, "8,14-dihydroxy-7,8-dihydrocodeinone," pp. 2-17, Aug. 19, 2004.
Search Report dated Jun. 10, 2010, in connection with Singaporean Application No. 2006052575.
Second Declaration of Professor Gilbert Stork, Ph.D. of Oct. 9, 2007.
Second Declaration of Steven W. Baldwin, Ph.D. of Oct. 3, 2007.
Sharapin N., "Fundamentos de Tecnologia de Productos Fitoterapeuticos," ano 2000.

(56) References Cited

OTHER PUBLICATIONS

Sharapin N., "Fundamentos de tecnologia de productos Fitoterapeuticos alio 2000"; (2000) pp. 81-82.
Sheet entitled "Communication from US FDA to Purdue Pharma L.P. and Rhodes Technologies in Jan. 2004 referred to in Section 18(1)(a)2(i)".
Skoog, D. A., West, D. M., Holler, F. J., Fundamentals of Analytical Chemistry, pp. 660-662, 682-684 and 774-775, ($7^{th}$ Ed.) (1996).
Statement of Grounds & Particulars filed in connection with Australian Application No. 2009200335 on Jan. 25, 2012.
Statutory Declaration by Christopher John Easton dated Mar. 7, 2014, filed in connection with Australian Patent No. 2005230826.
Statutory Declaration by Philip Andrew Marshall dated Jul. 30, 2013, including Exhibits PAMD-1 to PAMD-15, which was filed in connection with Australian divisional patent No. 2009200335 on Aug. 6, 2013.
Statutory Declaration by Philip Andrew Marshall dated Oct. 8, 2013, including Exhibits PAM-29 to PAM-38, which was filed in connection with Australian patent No. 2005230826 on Oct. 8, 2013.
Statutory Declaration No. 1 by Carol Margaret Burton dated Jul. 31, 2013, including Exhibits CMB-1 to CMB-10, which was filed in connection with Australian divisional patent No. 2009200335 on Aug. 6, 2013.
Statutory Declaration No. 2 by Carol Margaret Burton dated Jul. 31, 2013, including Exhibits CMB-11 to CMB-18, which was filed in connection with Australian divisional patent No. 2009200335 on Aug. 6, 2013.
Statutory Declaration of Carol Margaret Burnton dated Apr. 27, 2011, and filed in connection with Australian Patent Application No. 2005230826.
Statutory Declaration of Carol Margaret Burnton dated Jun. 21, 2011, and filed in connection with Australian Patent Application No. 2005230826.
Statutory Declaration of Carol Margaret Burnton in connection with Australian Patent Application No. 2005230826 dated Feb. 10, 2011.
Statutory Declaration of Paul William Jones dated Dec. 8, 2010, and filed in connection with Australian Patent Application No. 2005230826.
Statutory Declaration of Paul William Jones in connection of Australian Patent Application No. 2005230826 dated Dec. 8, 2010.
Statutory Declaration of Philip Andrew Marshall dated Apr. 18, 2011, and filed in connection with Australian Patent Application No. 2005230826.
Statutory Declaration of Philip Andrew Marshall dated Jun. 21, 2011, and filed in connection with Australian Patent Application No. 2005230826.
Statutory Declaration of Philip Marshall filed on Jul. 27, 2010, in connection with the opposition in corresponding Australian Application No. 2005230826.
Stephen P. Findlay & Lyndon F. Small, The Acid-catalyzed Conversion of Codeinone to 8-Hydroxydihydrocodeinone, 73 J. Am. Chem. Soc'y 4001 (1951).
Stewart A. W., Annual Reports on the Progress of Chemistry for 1919, Gurney & Jackson , p. 123.
Summons to attend oral proceedings issued in connection with corresponding European Application No. 05 730 348.5 on Nov. 5, 2012.
Temo Harano et al., 3a-Hydroxy-5 3,14 p-chol-8-en-24-oic Acid and its Isomer, Dehydration Products of Chenodeoxycholic Acid Obtained by Treatment with Concentrated HCl, 30 Steroids 393 (1977).
Teva Pharmaceuticals USA, Inc.'s Answer, Affirmative Defenses and Counterclaims to Complaint, *Purdue Pharma L.P., et al. v Teva Pharmaceuticals USA, Inc.*, C.A. No. 1:11-cv-02037-UA (SDNY 2011).
Teva Pharmaceuticals USA, Inc.'s First Amended Answer, Affirmative Defenses and Counterclaims to Complaint, *Purdue Pharma L.P., et al. v. Teva Pharmaceuticals USA, Inc.*, C.A. No. 1:11-cv-02037-UA (SDNY 2011).

The Communication pursuant to Article 94(3) EPC issued in connection with corresponding European Patent Application No. 10 011792.8 dated Jul. 21, 2014.
The FDA response to Citizen Petition on behalf of Endo Pharmaceuticals dated May 13, 2010, the response dated Nov. 8, 2010.
The Japanese Pharmacopoeia, $16^{th}$ edition, pp. 1196-1199 (2011).
The Notice of Final Rejection dated Feb. 28, 2013, by the Korean Patent Office, in connection with Korean Application No. 10-2012-7017379.
The Notice of Reasons for Rejection dated Feb. 19, 2013 by the Japanese Patent Office, in connection with Japanese Application No. 2011-251260.
The Office Action dated Apr. 17, 2013, in connection with Korean Patent Application No. 10-20137000989.
The Office Action dated Dec. 21, 2012 by the European Patent Office, in connection with European Application No. 10 011 793.6.
The Office Action dated Dec. 21, 2012 by the European Patent Office, in connection with European Application No. 10 011 787.8.
The Office Action dated Dec. 21, 2012 by the European Patent Office, in connection with European Application No. 10 011 788.6.
The Office Action dated Dec. 21, 2012 by the European Patent Office, in connection with European Application No. 11 186 168.8.
The Office Action dated Mar. 6, 2013, in connection with European Application No. 10 011 791.0.
The Office Action dated Mar. 6, 2013, in connection with European Patent Application No. 10011792.8.
Third Declaration of Professor Gilbert Stork, Ph.D. of Nov. 15, 2007.
Third Declaration of Steven W. Baldwin, Ph.D. of Nov. 15, 2007.
Third Party Observation filed in connection with corresponding European Patent Application No. 10 011792.8 on Jun. 13, 2014.
Third Party Observations filed in connection with corresponding European Application No. 10011791.02117/2311839 on Nov. 30, 2012.
Third Party Observations filed in connection with corresponding European Application No. 10011787.82117/2319846 on Nov. 30, 2012.
Third Party Observations filed in connection with corresponding European Application No. 10011788.62117-2316837 on Nov. 30, 2012.
Third Party Observations filed in connection with corresponding European Application No. 11186168.82117/2426132 on Nov. 30, 2012.
Transcript of Videotaped Deposition of Gilbert Stork Ph.D. of Sep. 18, 2007.
Transcript of Videotaped Deposition of Steven W. Baldwin, Ph.D. of Sep. 21, 2007.
Transcript of Videotaped Deposition of Steven W. Baldwin, Ph.D. of Oct. 31, 2007.
Transcript of Videotaped Deposition of Steven W. Baldwin, Ph.D. of Dec. 13, 2007.
Translation of submission by Opponent 3 (Acino Pharma AG) dated Jun. 13, 2013, filed in connection with corresponding European Patent No. 1 730 151.
U.S. Pharmacopeia, "Official Monograph for oxycodone hydrochloride", U.S. Pharmacopeia! Convention, May 1, 2015, pp. 4705-4707.
U.S. Pharmacopeia, "Official Monograph for oxycodone hydrochloride", U.S. Pharmacopeia! Convention, Jan. 1, 1995, pp. 1129-1134.
Ulrich Weiss, "Derivatives of Morphine," J. Am. Chem. Soc. 1955, v. 77, pp. 5891-5892, Nov. 20, 1955.
United States Pharmacopeia, USP 27, p. 1375, (2004).
Varam, Inc.'s Answer, Separate Defenses and Counterclaims, *Purdue Pharma L.P., et al. v. Varam Inc., et al.*, C.A. No. 10-cv-04028-PBT (EDPA 2010).
ViebOck F., *Oxydation des Thebians mit Manganiacetat*, Chem. Ber. 67, 197-202, 1934, including its English translation.
Vogel, A. I., Part 2: Qualitative Organic Analysis ($2^{nd}$ ed.) in 'Elementary Practical Organic Chemistry,' Longman Group Limited, p. 223-38 (1966).
Vogel's Textbook of Practical Organic Chemistry, pp. 89-90, and 133-153, 5th ed. (1989).

(56) References Cited

OTHER PUBLICATIONS

Walker, Adam, J., et al., "Combined Biological and Chemical Catalysts in the Preparation of Oxycodone", Tetrahedron, vol. 60, Nov. 2004, pp. 561-568.
*Webster's Third New International Dictionary of the English Language Unabridged*, 1993, pp. 1146 ("incubate") and 1815 ("promote").
Weiss, J. Org. Chem. (1957), pp. 1505-1508.

\* cited by examiner

Reaction scheme of the process used to produce oxycodone HCl from thebaine.

8a,14-dihydroxy-7,8-dihydrocodeinone    14-hydroxycodein

Dehydration of 8α, 14-dihydroxy-7,8-dihydrocodeinone

Typical HPLC Chromatogram of RTM Solution

Typical HPLC Chromatogram of the Working 100 PPM 14OHC Standard Solution

Typical HPLC Chromatogram of the Sample Solution containing Oxycodone API

PROCESS FOR PREPARING OXYCODONE COMPOSITIONS

CROSS REFERENCE TO RELATED APPLICATIONS

This application is a continuation of U.S. application Ser. No. 15/058,420, filed Mar. 2, 2016, now U.S. Pat. No. 9,777,011, which is a continuation of U.S. application Ser. No. 15/058,420, filed Mar. 2, 2016, which is a continuation of U.S. patent application Ser. No. 14/725,210, filed on May 29, 2015, which is a continuation of U.S. patent application Ser. No. 13/366,755, filed on Feb. 6, 2012, now U.S. Pat. No. 9,073,933, which is a continuation of U.S. patent application Ser. No. 12/893,681, filed on Sep. 29, 2010, which is a continuation of U.S. patent application Ser. No. 12/380,800, filed Mar. 4, 2009, which is a continuation of U.S. patent application Ser. No. 11/653,529, filed Jan. 16, 2007, which is a continuation of U.S. patent application Ser. No. 11/391,897, filed Mar. 29, 2006, which is a continuation of U.S. patent application Ser. No. 11/093,626, filed Mar. 30, 2005, now U.S. Pat. No. 7,129,248, which claims priority to U.S. Provisional Application No. 60/651,778, filed Feb. 10, 2005, U.S. Provisional Application No. 60/648,625, filed Jan. 31, 2005, U.S. Provisional Application No. 60/620,072, filed Oct. 18, 2004, U.S. Provisional Application No. 60/601,534, filed Aug. 13, 2004, and U.S. Provisional Application No. 60/557,492, filed Mar. 30, 2004, all of which are hereby incorporated by reference.

FIELD OF THE INVENTION

The present invention relates to a process for reducing the amount of 14-hydroxycodeinone in an oxycodone hydrochloride preparation.

BACKGROUND OF THE INVENTION

Oxycodone is a semi-synthetic opioid analgesic that exerts an agonist effect at specific, saturable opioid receptors in the CNS and other tissues. In man, oxycodone may produce any of a variety of effects including analgesia.

Purdue Pharma L. P currently sells sustained-release oxycodone in dosage forms containing 10, 20, 40, and 80 mg oxycodone hydrochloride under the trade name OxyContin®.

U.S. Pat. Nos. 5,266,331; 5,508,042; 5,549,912; and 5,656,295 disclose sustained release oxycodone formulations.

Thebaine, a compound derived from opium, although having no medicinal use in itself, is useful as a starting material in synthetic schemes for the production of oxycodone. In other schemes, codeine can be utilized as the starting material for the production of oxycodone. 14-hydroxycodeinone is the immediate precursor to oxycodone in these schemes.

Methods of producing thebaine or 14-hydroxy substituted opium derivatives have been reported, e.g. in U.S. Pat. Nos. 3,894,026 and 4,045,440.

The oxidation of codeine to codeinone, an initial step in the synthesis of opium derivatives has been reported in EP 0889045, U.S. Pat. No. 6,008,355 and in the J. Am. Chem. Soc., 1051, 73, 4001 (Findlay).

The reaction of codeinone to 14-hydroxycodeinone has been reported in U.S. Pat. No. 6,008,355 and in Tetrahedron 55, 1999 (Coop and Rice).

The methylation of codeinone to thebaine has been reported in Heterocycles, 1988, 49, 43-7 (Rice) and EP0889045.

U.S. Pat. No. 6,177,567 describes the hydrogenation of 14-hydroxycodeinone to oxycodone by reduction with diphenylsilane and Pd(Ph3P)/ZnCl2 or with sodium hypophosphite in conjunction with a Pd/C catalyst in aqueous acetic acid.

Krabnig et al. in "Optimization of the Synthesis of Oxycodone and 5-Methyloxycodone" Arch. Pharm. (1996), 329 (6), (325-326) describes hydrogenating a solution of 14-hydroxycodeinone in glacial acetic acid with a Pd—C-catalyst at 30 psi at the described conditions.

During the oxidation of thebaine to give 14-hydroxycodeinone, several overoxidized products are formed including 8,14-dihydroxy-7,8-dihydrocodeinone. In the production of oxycodone free base from the 14-hydroxycodeinone, the 8,14-dihydroxy-7,8-dihydrocodeinone is carried though the process. During conversion of the oxycodone free base to oxycodone hydrochloride, the impurity undergoes acid-catalyzed dehydration and is converted into 14-hydroxycodeinone. Thus, 14-hydroxycodeinone is present in the final oxycodone hydrochloride composition. Oxycodone hydrochloride API (active pharmaceutical ingredient) is available from a variety of manufacturers such as Johnson Matthey and Mallinckrodt. Current commercially-available oxycodone hydrochloride API, and oxycodone hydrochloride prepared by known procedures, have a level of 14-hydroxycodeinone of greater than 100 ppm.

There is a continuing need in the art to provide an oxycodone hydrochloride composition that contains reduced amounts of 14-hydroxycodeinone as compared to compositions known in the art.

All references cited herein are incorporated by reference in their entireties for all purposes.

OBJECTS AND SUMMARY OF THE INVENTION

It is an object of certain embodiments of the present invention to provide a process for reducing the 14-hydroxycodeinone in an oxycodone hydrochloride composition to an amount of less than 25 ppm, less than about 15 ppm, less than about 10 ppm, or less than about 5 ppm.

It is an object of certain embodiments of the present invention to provide a process for reacting an oxycodone base composition with hydrochloric acid under conditions to produce an oxycodone hydrochloride composition having an amount of 14-hydroxycodeinone of less than 25 ppm, less than about 15 ppm, less than about 10 ppm, or less than about 5 ppm.

It is a further object of certain embodiments of the present invention to provide an oxycodone hydrochloride composition having a 14-hydroxycodeinone level of less than 25 ppm, less than about 15 ppm, less than about 10 ppm, or less than about 5 ppm.

It is a further object of certain embodiments of the present invention to provide a process for preparing an oxycodone hydrochloride composition having a 14-hydroxycodeinone level of less than 25 ppm by reacting an oxycodone base composition with hydrochloric acid under conditions suitable to promote dehydration of 8,14-dihydroxy-7,8-dihydrocodeinone to 14-hydroxycodeinone during salt formation and under reducing conditions so as to convert the 14-hydroxycodeinone to oxycodone.

In certain embodiments, the invention is directed to a process for preparing an oxycodone hydrochloride composition having a 14-hydroxycodeinone level of less than 25 ppm comprising reacting an oxycodone hydrochloride composition having a 14-hydroxycodeinone level of more than 100 ppm under conditions that reduce the amount of 14-hydroxycodeinone to a level of less than 25 ppm, less than about 15 ppm, less than about 10 ppm, or less than about 5 ppm.

In certain embodiments, the invention is directed to an oxycodone hydrochloride composition having a 14-hydroxycodeinone level of less than 25 ppm, less than about 15 ppm, less than about 10 ppm, or less than about 5 ppm.

In certain embodiments, the invention is directed to a process for preparing an oxycodone hydrochloride composition having a 14-hydroxycodeinone level of less than 25 ppm comprising subjecting an oxycodone hydrochloride composition having a 14-hydroxycodeinone level of greater than 100 ppm to hydrogenation to an extent that the amount of 14-hydroxycodeinone in the composition is reduced to an amount of less than less 25 ppm, less than about 15 ppm, less than about 10 ppm, or less than about 5 ppm.

In certain embodiments disclosed herein, the oxycodone composition having a 14-hydroxycodeinone level of less than 25 ppm can be subsequently hydrogenated to further decrease the amount of 14-hydroxycodeinone, e.g., from about 15 ppm to about 10 ppm or less.

In one embodiment, where the starting material is an oxycodone hydrochloride composition comprising 14-hydroxycodeinone in an amount of 100 ppm or higher, the final oxycodone hydrochloride composition has a 14-hydroxycodeinone level of less than 25 ppm, less than about 15 ppm, less than about 10 ppm, or less than about 5 ppm. In another embodiment, where the starting material is an oxycodone hydrochloride composition comprising 14-hydroxycodeinone in an amount of between 15 ppm and 25 ppm, the final oxycodone hydrochloride composition has a 14-hydroxycodeinone level of less than about 10 ppm, or less than about 5 ppm. In another embodiment, where the starting material is an oxycodone hydrochloride composition comprising 14-hydroxycodeinone in an amount of between 10 ppm and 25 ppm, the final oxycodone hydrochloride composition has a 14-hydroxycodeinone level of less than about 5 ppm.

In certain embodiments of the present invention, the process for preparing the oxycodone hydrochloride composition having a 14-hydroxycodeinone level of less than 25 ppm comprises hydrogenating the starting material under reflux. In certain embodiments, the process further comprises recovering the resultant oxycodone hydrochloride composition having a 14-hydroxycodeinone level of less than 25 ppm.

In certain embodiments, the invention is directed to a process for preparing an oxycodone hydrochloride composition having a 14-hydroxycodeinone level of less than 25 ppm comprising hydrogenating under reflux, a starting oxycodone hydrochloride composition having a 14-hydroxycodeinone level of greater than 100 ppm in a suitable solvent for a time sufficient to produce an oxycodone composition having a 14-hydroxycodeinone level of less than 25 ppm, less than about 15 ppm, less than about 10 ppm, or less than about 5 ppm; and recovering the oxycodone hydrochloride composition having a 14-hydroxycodeinone level of less than 25 ppm by crystallization and removal from the solvent (e.g., by filtration).

In certain embodiments, the oxycodone hydrochloride composition of the present invention has a lower limit of 0.25 ppm, 0.5 ppm, 1 ppm, 2 ppm or 5 ppm of 14-hydroxycodeinone.

In certain embodiments, the invention is directed to a process for preparing an oxycodone hydrochloride composition having a 14-hydroxycodeinone level in an amount of less than 25 ppm comprising reacting in a suitable solvent an oxycodone base composition with hydrochloric acid in an amount greater than 1.0 molar equivalent as compared to the oxycodone base composition, the reacting step being performed under reducing conditions, to form an oxycodone hydrochloride composition having a 14-hydroxycodeinone level in an amount of less than 25 ppm.

In certain embodiments, the invention is directed to a process for preparing an oxycodone hydrochloride composition having less than 25 ppm 14-hydroxycodeinone comprising hydrogenating a 14-hydroxycodeinone composition to obtain an oxycodone free base composition; converting the oxycodone free base composition to oxycodone hydrochloride; and hydrogenating the oxycodone hydrochloride to obtain an oxycodone composition having less than 25 ppm 14-hydroxycodeinone.

In certain embodiments, the invention is directed to a process for preparing an oxycodone hydrochloride composition having less than 25 ppm 14-hydroxycodeinone comprising hydrogenating a 14-hydroxycodeinone composition to obtain an oxycodone free base composition; converting the oxycodone free base composition to oxycodone hydrochloride; isolating the oxycodone hydrochloride; and hydrogenating the oxycodone hydrochloride to obtain an oxycodone composition having less than 25 ppm 14-hydroxycodeinone.

In certain embodiments, the invention is directed to a process for preparing an oxycodone hydrochloride composition having less than 25 ppm 14-hydroxycodeinone comprising oxidizing a thebaine composition to form 14-hydroxycodeinone composition, the oxidizing being performed at a suitable pH to minimize or eliminate the production of 8,14-dihydroxy-7,8-dihydrocodeinone in the 14-hydroxycodeinone composition; hydrogenating the 14-hydroxycodeinone composition to form an oxycodone base composition; and converting the oxycodone base composition to an oxycodone hydrochloride composition having less than 25 ppm 14-hydroxycodeinone.

In certain embodiments, the invention is directed to a process for preparing 14-hydroxycodeinone comprising oxidizing a thebaine composition to form 14-hydroxycodeinone composition, the oxidizing being performed at a suitable pH to minimize or eliminate the production of 8,14-dihydroxy-7,8-dihydrocodeinone in the 14-hydroxycodeinone composition;

In certain embodiments, the invention is directed to a process for preparing an oxycodone hydrochloride composition comprising reacting an oxycodone base composition with an acid having a higher pH than hydrochloric acid to form a corresponding acid addition salt of oxycodone, and converting the acid addition salt of oxycodone to oxycodone hydrochloride.

In certain embodiments, the invention is directed to a process for preparing an oxycodone hydrochloride composition having a 14-hydroxycodeinone level in an amount of less than 25 ppm comprising contacting an oxycodone base composition having an amount of 8,14-dihydroxy-7,8-dihydrocodeinone with a substance that preferentially removes the 8,14-dihydroxy-7,8-dihydrocodeinone as compared to the oxycodone base; and converting the oxycodone base composition to an oxycodone hydrochloride composition having less than 25 ppm 14-hydroxycodeinone.

In certain embodiments, the invention is directed to a process for preparing an oxycodone hydrochloride composition having a 14-hydroxycodeinone level in an amount of less than 25 ppm comprising subjecting an oxycodone base composition having an amount of 8,14-dihydroxy-7,8-dihydrocodeinone to chromatographic separation to preferentially removes the 8,14-dihydroxy-7,8-dihydrocodeinone as compared to the oxycodone base; and converting the oxycodone base composition to an oxycodone hydrochloride composition having less than 25 ppm 14-hydroxycodeinone.

In certain embodiments, the invention is directed to a process for preparing an oxycodone hydrochloride composition having a 14-hydroxycodeinone level in an amount of less than 25 ppm comprising reacting in a suitable solvent an oxycodone base composition having an amount of 8,14-dihydroxy-7,8-dihydrocodeinone, with boronated polystyrene resin; and converting the oxycodone base composition to an oxycodone hydrochloride composition having less than 25 ppm 14-hydroxycodeinone.

In certain embodiments, the invention is directed to a process for preparing an oxycodone hydrochloride composition comprising reacting in a suitable solvent an oxycodone base composition with boronated polystyrene resin; and converting the oxycodone base composition to an oxycodone hydrochloride composition.

In certain embodiments, the invention is directed to a process for preparing an oxycodone hydrochloride composition having a 14-hydroxycodeinone level in an amount of less than 25 ppm comprising combining hydrochloric acid and an oxycodone base composition having an amount of 8,14-dihydroxy-7,8-dihydrocodeinone in a solvent to form a solution; and spray drying the solution to generate oxycodone hydrochloride composition having a 14-hydroxycodeinone level in an amount of less than 25 ppm.

In certain embodiments, the invention is directed to a process for preparing an oxycodone hydrochloride composition having a 14-hydroxycodeinone level in an amount of less than 25 ppm comprising combining hydrochloric acid and an oxycodone base composition having an amount of 8,14-dihydroxy-7,8-dihydrocodeinone in a solvent to form a solution; and lyophilizing the solution to generate oxycodone hydrochloride composition having a 14-hydroxycodeinone level in an amount of less than 25 ppm.

In certain embodiments, the invention is directed to a process for preparing an oxycodone hydrochloride composition comprising combining hydrochloric acid and an oxycodone base composition in a solvent to form a solution; and spray drying the solution to generate oxycodone hydrochloride.

In certain embodiments, the invention is directed to a process for preparing an oxycodone hydrochloride composition comprising combining hydrochloric acid and an oxycodone base composition in a solvent to form a solution; and lyophilizing the solution to generate oxycodone hydrochloride. The term "bulk" means an amount of material of at least 1 kg. In certain embodiments, the amount can be from about 10 kg to about 1000 kg or from about 10 kg to about 500 kg. In certain embodiments, the amount is in an amount of from about 20 kg to about 100 kg; about 20 kg or about 50 kg. Bulk oxycodone hydrochloride composition can be packaged, e.g., in a pharmaceutically acceptable package such as corrugated box containers (made of, e.g., plastic and/or paper); in drums (made of, e.g., a metal or metal composite material); or in bags of woven fabric generally referred to as flexible intermediate bulk containers (FIBCs). Each of these approaches use various configurations of liners, typically made of polyethylene or polypropylene, that fit within the corrugated box, drum, or within the FIBC for preventing contamination of the product being shipped. Preferably, these packaging approaches use containers configured to be supported by and carried on pallets.

The term "ppm" as used herein means "parts per million". As used to refer to 14-hydroxycodeinone, "ppm" means parts per million of 14-hydroxycodeinone in a particular sample.

The term 8,14-dihydroxy-7,8-dihydrocodeinone includes either 8α,14-dihydroxy-7,8-dihydrocodeinone; or 8β,14-dihydroxy-7,8-dihydrocodeinone or can include a mixture of both compounds.

The oxycodone hydrochloride preparation can be, e.g., an oxycodone active pharmaceutical ingredient (API), such as oxycodone hydrochloride U.S.P., uncombined or combined with one or more other ingredients. For example, the oxycodone preparation can be a final pharmaceutical dosage form, or an intermediate preparation for a final dosage form, that can be tested for the presence of 14-hydroxycodeinone and/or codeinone, e.g., for quality assurance purposes. Preferably, the oxycodone hydrochloride preparation is oxycodone hydrochloride API and contains at least 95% oxycodone hydrochloride, at least 98% oxycodone hydrochloride, at least 99% oxycodone hydrochloride, or at least 99.9% oxycodone hydrochloride.

The method of detecting the presence of 14-hydroxycodeinone in an oxycodone preparation can be performed in accordance with commonly assigned U.S. Provisional Application Ser. No. 60/557,502, entitled "Methods For Detecting 14-Hydroxycodeinone" filed Mar. 29, 2004 and in accordance with U.S. Provisional Application entitled "Methods For Detecting 14-Hydroxycodeinone" filed Jan. 31, 2005.

DETAILED DESCRIPTION

Figure 1:
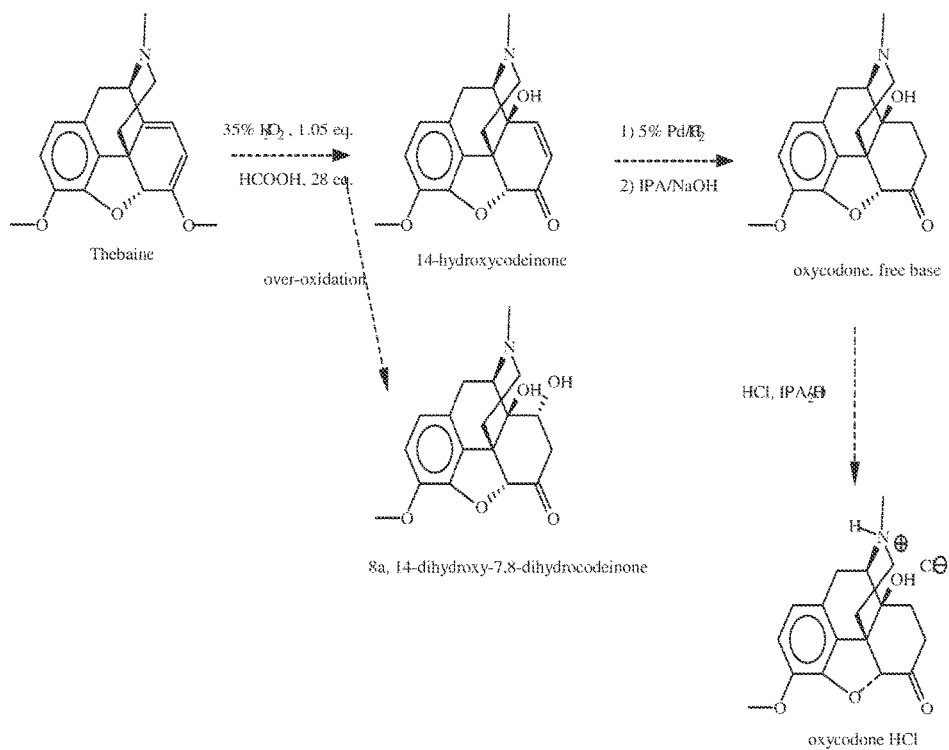
FIG. 1 is a schematic of a reaction of thebaine to oxycodone hydrochloride, including the oxidation of thebaine to 14-hydroxycodeinone and the 8,14-dihydroxy-7,8-dihydrocodeinone impurity.
Figure 2:
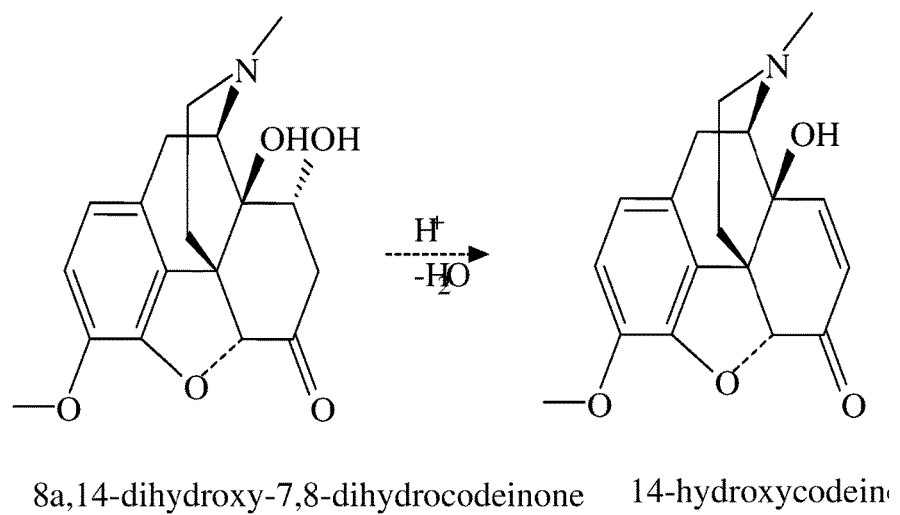
FIG. 2 is a schematic of the dehydration of 8,14-dihydroxy-7,8-dihydrocodeinone to 14-hydroxycodeinone.

In certain embodiments, the invention is directed to a process for reducing the amount of 14-hydroxycodeinone in an oxycodone hydrochloride composition (e.g., oxycodone hydrochloride API), and to the resultant oxycodone hydrochloride composition having a 14-hydroxycodeinone level of less than 25 ppm recovered from that process. In certain embodiments, the present invention is directed to a process for reducing the amount of 14-hydroxycodeinone in an oxycodone hydrochloride composition comprising reacting the oxycodone hydrochloride composition with a catalytically effective amount of a transition metal compound and a gas comprising hydrogen, at a temperature and for a period of time sufficient to reduce the content of 14-hydroxycodeinone to a level wherein the resultant oxycodone hydrochloride composition comprises 14-hydroxycodeinone in an amount less than 25 ppm, less than about 15 ppm; less than about 10 ppm, or less than about 5 ppm.

The process of the present invention also may result in the reduction of other alpha, beta, unsaturated ketones in oxycodone compositions, in addition to 14-hydroxycodeinone such as, e.g., codeinone.

In accordance with certain embodiments of the present invention, an oxycodone hydrochloride composition (e.g., oxycodone hydrochloride API), and a solvent, are fed into a reaction apparatus. The composition is then hydrogenated under adequate conditions for a sufficient period; the catalyst is removed from the solvent; and the oxycodone hydrochloride composition having a 14-hydroxycodeinone level of less than 25 ppm is isolated and removed, e.g., by crystallization and filtration.

Hydrogenation of the 14-hydroxycodeinone in the processes of the present invention can be accomplished by using, e.g., pressurized-catalytic hydrogenation or catalytic transfer hydrogenation in an appropriate acid, e.g., acetic acid. A particular hydrogenation reaction employs hydrogen gas or $NaHPO_2$ along with a palladium-carbon catalyst. In certain embodiments, a hydrogen donor for use in the hydrogenation of the 14-hydroxycodeinone can be selected from hydrogen, primary and secondary alcohols, primary and secondary amines, carboxylic acids and their esters and amine salts, readily dehydrogenatable hydrocarbons (e.g., lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnaphthalene, and diethylnaphthalene; paraffins such as ethane, propane, n-butane, isobutane, n-pentane, isopentane, n-hexane, n-heptane, n-octane, n-nonane, n-decane, and branched chain isomers thereof; cycloparaffins such as cyclobutane, cyclopentane, cyclohexane, methylcyclopentane, methylcyclohexane, and ethylcyclopentane; olefins such as ethylene, propylene, 1-butene, 2-butene, 1-pentene, 2-pentene, 1-hexene, 2-hexene, 3-hexene, and branched chain derivatives thereof), clean reducing agents (e.g., polymer-supported organotin hydrides, and any suitable combination thereof. In certain embodiments, the hydrogenation can be performed as disclosed in U.S. Provisional Application No. 60/477,968, filed Jun. 12, 2003, entitled "Hydrogenation of Opioids Without Hydrogen Gas Feed."

In certain embodiments, the hydrogenation is carried out at a pressure from about 5 PSIG to about 200 PSIG, or from about 40 PSIG to about 60 PSIG. In certain embodiments, the hydrogenation is carried out at a temperature of from about 20° C. to about 100° C., or from about 40° C. to about 85° C.

In certain embodiments, the hydrogenation is carried out at a pH of less than 5, less than 3, or less than 1, e.g., about 0.5.

In certain embodiments of the present invention, the 14-hydroxycodeinone is converted to oxycodone by hydrogenation utilizing diphenylsilane and $Pd(Ph_3P)/ZnCl_2$ and sodium hypophosphite in conjunction with a Pd/C catalyst in aqueous organic acid; or Pd/C catalytic transfer hydrogenation.

The total reaction time of the hydrogenation reaction is for a duration sufficient to reduce the content of the 14-hydroxycodeinone to a level that is less than 25 ppm, less than about 15 ppm, less than about 10 ppm, or less than about 5 ppm. The actual reaction time can vary depending upon the temperature and efficiency of the hydrogenation system. Depending on the hydrogenation conditions (e.g., temperature and pressure), the total reaction time to achieve the desired reduction in 14-hydroxycodeinone can be, e.g., from about 10 minutes to about 36 hours. The hydrogenation of the 14-hydroxycodeinone can be carried out in the presence of a noble metal catalyst. In certain embodiments, suitable catalysts can be selected from Raney cobalt, Raney nickel, palladium on carbon, platinum on carbon, palladium on alumina, platinum oxide, ruthenium on alumina, rhodium on alumina, or rhodium on carbon, among others. One particular catalyst for this reduction is 5% palladium on carbon. The quantity of palladium on carbon catalyst can be from about 0.05% w/w to about 50% w/w, or from about 0.5% w/w to about 5%, in relation to the treated composition.

The reaction may be carried out in a solvent such as water; an alcohol (such as, e.g., isopropanol, methanol or ethanol); tetrahydrofuran; an aromatic hydrocarbon (such as benzene); an ether (such as dioxane); an ester of a lower alkanoic acid (such as methyl acetate or ethyl acetate); an amide (such as, e.g., dimethylformamide, diethylformamide, dimethylacetomide, or other N-alkyl substituted lower fatty acid amides); N-methylpyrrolidone; formylmorpholine; β-methoxypropionitrile; a carboxylic acid (such as formic, acetic, propionic acid or other lower alkanoic acid) or an appropriate mixture of any two or more of the aforementioned solvents. One particular co-solvent combination is isopropanol/water.

In certain embodiments, the solvent is typically mixed with the 14-hydroxycodeinone-containing composition (e.g., an oxycodone composition) prior to hydrogenation.

In certain embodiments, the invention is directed to the conversion of an oxycodone free base composition (with an 8,14-dihydroxy-7,8-dihydrocodeinone component) to oxycodone hydrochloride. During salt formation reactions known in the art, the 8,14-dihydroxy-7,8-dihydrocodeinone component is converted to 14-hydroxycodeinone by acid-catalyzed dehydration. Thus, 14-hydroxycodeinone is increased in the final product. By virtue of the present invention, this can be reduced by overloading the amount of hydrochloric acid in the salt formation to promote the reaction of 8,14-dihydroxy-7,8-dihydrocodeinone to 14-hydroxycodeinone and providing reducing conditions sufficient for the 14-hydroxycodeinone to be readily converted to oxycodone. In such an embodiment, the amount of hydrochloric acid is an amount of greater than 1 molar equivalent as compared to the oxycodone free base. In certain embodiments, the molar equivalent amount of hydrochloric acid can be greater than about 1.2 molar equivalents or greater than about 1.4 molar equivalents. In certain embodiments, the amount of hydrochloric acid can be about 1.5 molar equivalents. The reducing conditions sufficient to drive the 14-hydroxycodeinone to oxycodone can be provided, e.g., by a catalyst with a hydrogen donor.

Further, during salt formation, the rate of dehydration of 8,14-dihydroxy-7,8-dihydrocodeinone to 14-hydroxycodeinone is reduced as the pH of the solution increases. Therefore, in certain embodiments, the pH of the solution can be adjusted to a pH of from about 1.5 to about 2.5, preferably to about 1.8, (e.g., from a pH of less than 1) with a suitable basic agent, e.g., sodium hydroxide. This further minimizes the formation of 14-hydroxycodeinone from 8,14-dihydroxy-7,8-dihydrocodeinone during crystallization. Preferably, the pH adjustment is performed after the hydrogenation step and prior to removal of catalyst and isolation of the oxycodone having a 14-hydroxycodeinone level of less than 25 ppm.

In certain embodiments it may be necessary to perform the process of the present invention, or one or more relevant steps in the process of the present invention, more than once in order to reduce the amount of 14-hydroxycodeinone to a desired level, e.g., less than about 10 ppm, or less than about 5 ppm.

In certain embodiments of the present invention, oxycodone hydrochloride compositions can be prepared by certain alternative processes. Such alternative processes preferably result in an oxycodone hydrochloride composition having a 14-hydroxycodeinone level in an amount of less than 25 ppm. One such alternative process is directed to a process for preparing an oxycodone hydrochloride composition having less than 25 ppm 14-hydroxycodeinone comprising oxidizing a thebaine composition to form 14-hydroxycodeinone composition, the oxidizing being performed at a suitable pH to minimize or eliminate the production of 8,14-dihydroxy-7,8-dihydrocodeinone in the 14-hydroxycodeinone composition; hydrogenating the 14-hydroxycodeinone composition to form an oxycodone base composition; and converting the oxycodone base composition to an oxycodone hydrochloride composition having less than 25 ppm 14-hydroxycodeinone.

Another alternative process is directed to a process for preparing 14-hydroxycodeinone comprising oxidizing a thebaine composition to form a 14-hydroxycodeinone composition, the oxidizing being performed at a suitable pH to minimize or eliminate the production of 8,14-dihydroxy-7,8-dihydrocodeinone in the 14-hydroxycodeinone composition.

Another alternative process is directed to a process for preparing an oxycodone hydrochloride composition comprising reacting an oxycodone base composition with an acid having a higher pH than hydrochloric acid to form a corresponding acid addition salt of oxycodone, and converting the acid addition salt of oxycodone to oxycodone hydrochloride. In such an embodiment, the acid may be selected from the group consisting of tartaric acid, oxalic acid, fumaric acid, phosphoric acid, sulfuric acid and mixtures thereof.

Another alternative process is directed to a process for preparing an oxycodone hydrochloride composition having a 14-hydroxycodeinone level in an amount of less than 25 ppm comprising contacting an oxycodone base composition having an amount of 8,14-dihydroxy-7,8-dihydrocodeinone with a substance that preferentially removes the 8,14-dihydroxy-7,8-dihydrocodeinone as compared to the oxycodone base; and converting the oxycodone base composition to an oxycodone hydrochloride composition having less than 25 ppm 14-hydroxycodeinone. In preferred embodiments the contacting substance can be a gel. In further embodiments, the contacting can comprise passing a solution comprising the oxycodone base composition through the substance or can comprise forming a slurry with the oxycodone base composition and the gel.

Another alternative process is directed to a process for preparing an oxycodone hydrochloride composition having a 14-hydroxycodeinone level in an amount of less than 25 ppm comprising subjecting an oxycodone base composition having an amount of 8,14-dihydroxy-7,8-dihydrocodeinone to chromatographic separation to preferentially remove the 8,14-dihydroxy-7,8-dihydrocodeinone as compared to the oxycodone base; and converting the oxycodone base composition to an oxycodone hydrochloride composition having less than 25 ppm 14-hydroxycodeinone. In preferred embodiments, the chromatographic separation is a simulated moving bed.

Another alternative process is directed to a process for preparing an oxycodone hydrochloride composition having a 14-hydroxycodeinone level in an amount of less than 25 ppm comprising contacting an oxycodone hydrochloride composition having an amount of 14-hydroxycodeinone with a substance that preferentially removes the 14-hydroxycodeinone as compared to the oxycodone hydrochloride; and recovering an oxycodone hydrochloride composition having less than 25 ppm 14-hydroxycodeinone. In preferred embodiments the contacting substance can be a gel. In further embodiments, the contacting can comprise passing a solution comprising the oxycodone hydrochloride composition through the substance or can comprise forming a slurry with the oxycodone hydrochloride composition and the gel.

Another alternative process is directed to a process for preparing an oxycodone hydrochloride composition having a 14-hydroxycodeinone level in an amount of less than 25 ppm comprising subjecting an oxycodone hydrochloride composition having an amount of 14-hydroxycodeinone to chromatographic separation to preferentially remove the 14-hydroxycodeinone as compared to the oxycodone hydrochloride; and recovering an oxycodone hydrochloride composition having less than 25 ppm 14-hydroxycodeinone. In preferred embodiments, the chromatographic separation is a simulated moving bed.

Another alternative process is directed to a process for preparing an oxycodone hydrochloride composition having a 14-hydroxycodeinone level in an amount of less than 25 ppm comprising reacting in a suitable solvent an oxycodone base composition having an amount of 8,14-dihydroxy-7,8-dihydrocodeinone, with boronated polystyrene resin; and converting the oxycodone base composition to an oxycodone hydrochloride composition having less than 25 ppm 14-hydroxycodeinone. Preferably the reacting is performed at a temperature below about 20 degrees C.

Another alternative process is directed to a process for preparing an oxycodone hydrochloride composition comprising reacting in a suitable solvent an oxycodone base composition with boronated polystyrene resin; and converting the oxycodone base composition to an oxycodone hydrochloride composition. Preferably the reacting is performed at a temperature below about 20 degrees C.

Another alternative process is directed to a process for preparing an oxycodone hydrochloride composition having a 14-hydroxycodeinone level in an amount of less than 25 ppm comprising combining hydrochloric acid and an oxycodone base composition having an amount of 8,14-dihydroxy-7,8-dihydrocodeinone in a solvent to form a solution; and spray drying the solution to generate oxycodone hydrochloride composition having a 14-hydroxycodeinone level in an amount of less than 25 ppm.

Another alternative process is directed to a process for preparing an oxycodone hydrochloride composition having a 14-hydroxycodeinone level in an amount of less than 25 ppm comprising combining hydrochloric acid and an oxycodone base composition having an amount of 8,14-dihydroxy-7,8-dihydrocodeinone in a solvent to form a solution; and lyophilizing the solution to generate oxycodone hydrochloride composition having a 14-hydroxycodeinone level in an amount of less than 25 ppm.

Another alternative process is directed to a process for preparing an oxycodone hydrochloride composition comprising combining hydrochloric acid and an oxycodone base composition in a solvent to form a solution; and spray drying the solution to generate oxycodone hydrochloride.

Another alternative process is directed to a process for preparing an oxycodone hydrochloride composition comprising combining hydrochloric acid and an oxycodone base composition in a solvent to form a solution; and lyophilizing the solution to generate oxycodone hydrochloride.

Further Embodiments

The oxycodone hydrochloride having a 14-hydroxycodeinone level of less than 25 ppm can be incorporated into pharmaceutical dosage forms, e.g., by admixtures of the oxycodone hydrochloride having a 14-hydroxycodeinone level of less than 25 ppm with conventional excipients, i.e., pharmaceutically acceptable organic or inorganic carrier substances. For oral formulations, the dosage forms can provide a sustained release of the active. Suitable pharmaceutically acceptable carriers include but are not limited to, alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, disintegrants, preservatives, stabilizers, wetting agents, emulsifiers, salts for influencing osmotic pressure buffers, coloring, flavoring and/or aromatic substances and the like. The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent. The oral dosage forms of the present invention may be in the form of tablets (sustained release and/or immediate release), troches, lozenges, powders or granules, hard or soft capsules, microparticles (e.g., microcapsules, microspheres and the like), buccal tablets, suppositories, solutions, suspensions, etc.

In certain embodiments, the present invention provides for a method of treating pain by administering to a human patient the dosage forms described herein.

When the dosage form is oral, the dosage form of the present invention contains from about 10 mg to about 320 mg of oxycodone hydrochloride having a 14-hydroxycodeinone level of less than 25 ppm. Particularly preferred dosages for twice daily dosing are about 5 mg, about 10 mg, about 15 mg, about 20 mg, about 30 mg, about 40 mg, about 50 mg, about 60 mg, about 80 mg, about 100 mg, or about 160 mg. Particularly preferred dosages for once daily dosing are about 10 mg, about 20 mg, about 30 mg, about 40 mg, about 60 mg, about 80 mg, about 100 mg, about 120 mg, about 160 mg, or about 320 mg. The oxycodone hydrochloride having a 14-hydroxycodeinone level of less than 25 ppm can also be formulated with suitable pharmaceutically acceptable excipients to provide a sustained release of the oxycodone hydrochloride having a 14-hydroxycodeinone level of less than 25 ppm. Such formulations can be prepared in accordance with U.S. Pat. Nos. 5,266,331; 5,508,042; 5,549,912; and 5,656,295.

The oxycodone hydrochloride having a 14-hydroxycodeinone level of less than 25 ppm can be formulated as a sustained release oral formulation in any suitable tablet, coated tablet or multiparticulate formulation known to those skilled in the art. The sustained release dosage form may include a sustained release material which is incorporated into a matrix along with the oxycodone or salt thereof.

The sustained release dosage form may optionally comprise particles containing oxycodone having a 14-hydroxycodeinone level of less than 25 ppm. In certain embodiments, the particles have a diameter from about 0.1 mm to about 2.5 mm, preferably from about 0.5 mm to about 2 mm. Preferably, the particles are film coated with a material that permits release of the active at a sustained rate in an aqueous medium. The film coat is chosen so as to achieve, in combination with the other stated properties, desired release properties. The sustained release coating formulations of the present invention should preferably be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose when ingested and contacted by an environmental fluid, e.g., gastric fluid or dissolution media.

The sustained release bead formulations of the present invention slowly release the active of the present invention, e.g., when ingested and exposed to gastric fluids, and then to intestinal fluids. The sustained release profile of the formulations of the invention can be altered, for example, by varying the amount of overcoating with the hydrophobic material, altering the manner in which a plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with the agent(s) of the present are prepared, e.g., by dissolving the agent(s) in water and then spraying the solution onto a substrate, for example, nu pariel 18/20 beads, using a Wuster insert. Optionally, additional ingredients are also added prior to coating the beads in order to assist the binding of the active to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the active(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer.

Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the agent(s) by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined sustained release of the agent(s) when the coated substrate is exposed to aqueous solutions, e.g. gastric fluid, may be applied. After coating with the hydrophobic material, a further overcoat of a film-former, such as Opadry®, is optionally applied to the beads. This overcoat is provided, if at all, in order to substantially reduce agglomeration of the beads.

The release of the agent(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,8989; 4,063,064; and 4,088,864.

Matrix Formulations

In other embodiments of the present invention, the sustained release formulation is achieved via a matrix optionally having a sustained release coating as set forth herein. The materials suitable for inclusion in a sustained release matrix may depend on the method used to form the matrix.

For example, a matrix in addition to the oxycodone hydrochloride having a 14-hydroxycodeinone level of less than 25 ppm may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting sustained release of the agent(s) and which melts (or softens to the extent necessary to be extruded) may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 2530° to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax.

For purposes of the present invention, a wax-like substance is defined as any material which is normally solid at room temperature and has a melting point of from about 25° to about 100° C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of oxycodone hydrochloride release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioidoxycodone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g. diluents, lubricants, binders, granulating aids, colorants, flavorants and glidants that are conventional in the pharmaceutical art.

Matrix—Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and the oxycodone hydrochloride having a 14-hydroxycodeinone level of less than 25 ppm; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose granules with water.

In yet other alternative embodiments, a spheronizing agent, together with the active can be spheronized to form spheroids. Microcrystalline cellulose is a preferred spheronizing agent. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the oxycodone hydrochloride having a 14-hydroxycodeinone level of less than 25 ppm together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, the oxycodone hydrochloride having a 14-hydroxycodeinone level of less than 25 ppm, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681 (Klimesch, et. al.), described in additional detail above.

Optionally, the sustained release melt-extruded multiparticulate systems or tablets can be coated, or the gelatin capsule containing the multiparticulates can be further coated, with a sustained release coating such as the sustained release coatings described above. Such coatings preferably include a sufficient amount of hydrophobic material to obtain a weight gain level from about 2 to about 30 percent, although the overcoat may be greater depending upon the desired release rate, among other things.

The melt-extruded unit dosage forms of the present invention may further include combinations of melt-extruded particles before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the oxycodone hydrochloride having a 14-hydroxycodeinone level of less than 25 ppm, which can be added thereafter to the extrudate. Such formulations typically will have the agents blended together with the extruded matrix material, and then the mixture would be tableted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the active in desired areas of the gastro-intestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the oxycodone hydrochloride having a 14-hydroxycodeinone level of less than 25 ppm thereof is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493.

Other examples of sustained release formulations and coatings which may be used in accordance with the present invention include those described in U.S. Pat. Nos. 5,324, 351; 5,356,467, and 5,472,712.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (containing the oxycodone hydrochloride having a 14-hydroxycodeinone level of less than 25 ppm) and a delivery or push layer, wherein the bilayer core is surrounded by a semipermeable wall and optionally having at least one passageway disposed therein.

The expression "passageway" as used for the purpose of this invention, includes aperture, orifice, bore, pore, porous element through which oxycodone hydrochloride having a 14-hydroxycodeinone level of less than 25 ppm can be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly (vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The dosage form can be manufactured with one or more passageways in spaced-apart relation on one or more surfaces of the dosage form. A passageway and equipment for forming a passageway are disclosed in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are disclosed in U.S. Pat. Nos. 4,200,098 and 4,285,987.

In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly (ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the oxycodone hydrochloride having a 14-hydroxycodeinone level of less than 25 ppm thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a homogenous core comprising oxycodone hydrochloride having a 14-hydroxycodeinone level of less than 25 ppm, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the oxycodone hydrochloride having a 14-hydroxycodeinone level of less than 25 ppm.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm$^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

In certain preferred embodiments, the present invention includes a therapeutic composition comprising an amount of oxycodone hydrochloride having a 14-hydroxycodeinone level of less than 25 ppm equivalent to 10 to 40 mg oxycodone hydrochloride, 25 to 500 mg of poly(alkylene oxide) having a 150,000 to 500,000 average molecular weight, 1 to 50 mg of polyvinylpyrrolidone having a 40,000 average molecular weight, and 0 to about 7.5 mg of a lubricant.

Suppositories

The sustained release formulations of the present invention may be formulated as a pharmaceutical suppository for rectal administration comprising a suitable suppository base, and oxycodone hydrochloride having a 14-hydroxycodeinone level of less than 25 ppm. Preparation of sustained release suppository formulations is described in, e.g., U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionization, and lipid solubility.

The suppository base chosen should be compatible with the active of the present invention. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent by weight of the total weight of the suppository. Preferably, the amount of suppository base in the suppository is from about 65 percent to about 80 percent, by weight of the total weight of the suppository.

Additional Embodiments

The oxycodone hydrochloride having a 14-hydroxycodeinone level of less than 25 ppm may be used as a substitute for the oxycodone hydrochloride in any existing commercial product such as, e.g., Tylox®, Roxilox®, Roxicet®, Percocet®, Oxycet®, Percodan®, Roxycodone®, OxyContin® and OxyIR®. Such formulations are listed in the PDR 58th Edition (2004) and the FDA Orange Book.

The following examples illustrate various aspects of the present invention. They are not to be construed to limit the claims in any manner whatsoever.

Example 1

In Example 1, 37.7 g of oxycodone HCl (35.4 g dry basis, ca. 500 ppm 14-hydroxycodeinone) was placed in a 500 mL Parr reaction bottle and combined with 0.55 g 5% Pd/C catalyst, 50% water wet (Johnson Matthey type 87L), and 182.2 g of 61.9% isopropanol/water (w/w). The mixture was placed under an inert atmosphere and heated with shaking to 45-50° C. Upon dissolution of all starting material, the pressure in the bottle was vented to the atmosphere and hydrogen pressure was applied (45 PSIG) for 4 hours. At the end of the hydrogenation, the hydrogen was vented off and the solution was allowed to cool to room temperature.

The next day, the mixture was heated to 75° C. to dissolve the crystallized solids and then suction filtered over a 0.2 μm PTFE membrane into a 1 L jacketed cylindrical flask (equipped with a condenser, a nitrogen atmosphere, a mechanical stirrer, a type K thermocouple, and a programmable refrigerated recirculator). The Parr bottle was rinsed with deionized water (11.7 g), which was added to the 1 L flask through the filter. Isopropanol (334.7 g) was added to the flask and the mixture was re-heated with stirring to 75° C. and held to dissolve any crystallized solids. The solution was cooled with stirring to 0-10° C. over 8 hours (linear ramp) and held at 0-10° C. for 20 hours. The crystallized solid was then collected by suction filtration and washed with 107 g of cold 95:5 isopropanol/water (w/w).

To remove isopropanol from product, the solvent-wet material was transferred to a drying dish and placed in a vacuum desiccator with an open container of deionized water. The solid was held in this manner, under vacuum, overnight. The material was then dried under vacuum at 60° C.

Analysis of the dried material using the low 14-hydroxycodeinone method of Example 4 below gave a result of 6 ppm of 14-hydroxycodeinone.

Analysis of the dried material using the method of Example 6 below gave a result of <5 ppm of codeinone and 8 ppm of 14-hydroxycodeinone.

Example 2

In Example 2, 35.0 g of oxycodone HCl (33.3 g dry basis, ca. 4000 ppm 14-hydroxycodeinone) was placed in a 500 mL Parr reaction bottle and combined with 0.49 g 5% Pd/C catalyst, 50% water wet (Johnson Matthey type 87L), and 159.9 g of 62.3% isopropanol/water. The mixture was placed under an inert atmosphere and then heated with shaking to 45-50° C. Upon dissolution of the starting material, the pressure in the bottle was vented to the atmosphere and hydrogen pressure was applied (45 PSIG). After 5.25 hours of shaking, the hydrogen was vented off, and the solution was allowed to cool to room temperature. The mixture was re-heated the next day and hydrogenation was continued for 4.75 hours.

The mixture was heated to 75° C. and then suction filtered over a 0.2 μm PTFE membrane into a 1 L jacketed cylindrical flask (equipped with a distillation head, a nitrogen atmosphere, a mechanical stirrer, a type K thermocouple, and a programmable refrigerated recirculator). The Parr bottle was rinsed with deionized water (11.7 g), which was added to the 1 L flask through the filter.

Isopropanol (295.6 g) was added to the flask and the mixture was heated to boiling (ca. 81° C.). To remove water and increase the yield, isopropanol/water azeotrope was distilled from the flask until 305.7 g had been collected. Fresh isopropanol (305.6 g) was added and the distillation head was removed and replaced with a condenser.

The mixture was cooled with stirring from boiling to 0-10° C. over 8 hours (linear ramp) and held at 0-10° C. for 20 hours. The crystallized solid was then collected by suction filtration and washed with 107 g of cold 95:5 isopropanol/water. The material was dried as described in Example 1.

Analysis of the dried material using the low 14-hydroxycodeinone method of Example 4 below gave a result of <5 ppm of 14-hydroxycodeinone.

Analysis of the dried material using the method of Example 6 below gave a result of <5 ppm of codeinone and <5 ppm of 14-hydroxycodeinone.

Example 3

In Example 3, 27.83 g of oxycodone free-base, water wet (24.57 g dry basis, 0.0779 mol, ca. 3000 ppm 14-hydroxycodeinone), 39.8 g of deionized water, 81.9 g of isopropanol, 0.49 g 5% Pd/C catalyst, 50% water wet (Johnson Matthey type 87L), and conc. HCl (11.3 g, 0.117 mol, 1.50 equivalents based on 37.7% HCl assay) were combined in a 500 ml Parr shaker bottle.

The mixture was placed under an inert atmosphere and heated to 75° C. with shaking. The pressure in the bottle was relieved, and the system was pressurized with hydrogen (45 PSIG). The solution was held under these conditions for 21.7 hours. Analysis by HPLC showed that the ratio of the area of the 8,14-dihydroxy-7,8-dihydrocodeinone peak to that of oxycodone was reduced from 0.29% to 0.04% during this time.

The hydrogen pressure was vented and the system was placed under an inert atmosphere. In order to prevent further dehydration of any residual 8,14-dihydroxy-7,8-dihydrocodeinone, the pH of the solution was adjusted from 0.5 to 1.8 with 20.7 g NaOH saturated isopropanol (some solid sodium hydroxide was also present).

The solution was re-heated to 75° C. and then pressure filtered through a 0.2 μm PTFE membrane filter housed in heat-traced 47 mm SS filter holder into a 500 ml jacketed cylindrical reactor (condenser, $N_2$, mechanical stirrer, programmable refrigerated recirculator). The Parr bottle was rinsed with 8.6 g of deionized water, which was added to the flask through the filter.

Isopropanol (222.5 g) was added to the solution in the flask and the resulting slurry was heated to approximately 75° C. to re-dissolve the solids. After reaching the desired temperature, the solution was held for two hours (to simulate typical processing times). No 14-hydroxycodeinone was detected in a sample of the crystallization mixture after this hold.

The circulator was set to cool from 80° C. to 0° C. over 8 hours. Approximately 24 hours after starting the cooling program, the solids were collected by suction filtration and washed three times with 95:5 isopropanol/water (232.8 g total). The material was dried as described in Example 1.

Analysis of the dried material using the low 14-hydroxycodeinone method of Example 4 below gave a result of 5 ppm of 14-hydroxycodeinone.

Analysis of the dried material using the method of Example 6 below gave a result of <5 ppm of codeinone and 10 ppm of 14-hydroxycodeinone.

Example 4

Analysis of sample to determine 14-hydroxycodeinone level.

The products of Examples 1-3 were analyzed to determine the level of 14-hydroxycodeinone under 100 parts per million (PPM) level by a HPLC method using a Waters Atlantis 5 μm dC18, 3×250 mm column maintained at 50° C. and isocratic elution using pH 9.35, 17 mM ammonium carbonate buffer and methanol (60:40). Quantitation was achieved by measuring the peak area response with UV detection at 220 nm using external standard. This method utilized mobile phase with volatile components that are compatible with LC/MS analysis.

The reagents used were as follows:
1. Ammonium carbonate, analytical reagent grade (Aldrich);
2. Water, HPLC grade;
3. Methanol, HPLC grade;
4. Acetic acid, reagent grade (J. T Baker Glacial Acetic Acid);
5. Ammonium hydroxide, reagent grade;
6. Phosphoric acid, about 85%, A.C.S. reagent;
7. 14-Hydroxycodeinone reference material from Albany Molecular Research, Inc.

The equipment used was as follows:
A. HPLC System
1. HPLC system capable of delivering 0.4 mL/minute of mobile phase (Waters Alliance);
2. UV/Visible detector set to monitor the eluant at 220 nm (Waters 2487 UV/Vis);
3. Autosampler capable of injecting 6 μL;
4. Integrator or suitable data recording system (Waters Millennium 32 chromatograph system.);
5. Waters, Atlantis dC18 column, 3×250 mm, 5 μm;
6. Column heater capable of maintaining a constant temperature of 50° C.;
7. On-line vacuum degasser.
B. Equipment for Mobile Phase Preparation
1. pH meter, preferably with automatic temperature compensation (ATC);
2. Ultrasonic bath, Model 5200, Branson;
3. 0.45-μm membrane filters for aqueous solvent, Whatman or Millipore, Cellulose acetate or Nylon.

Solutions 17 mM Ammonium carbonate, pH 9.35
1.6±0.1 g of ammonium carbonate was weighed and placed into a 1-L beaker. 1000 mL of water was added to the beaker and stirred with a magnetic stirrer until the ammonium carbonate was dissolved. The pH was adjusted to 9.35-9.40 with ammonium hydroxide.

B. Mobile Phase
400 mL of HPLC-grade methanol was mixed with 600 mL of 17 mM ammonium carbonate, pH 9.35-9.40 prepared above. The mixture was filtered through solvent membrane filters and then degassed using an on-line vacuum degasser in the HPLC system.

C. 0.85% Phosphoric Acid Solution
10.0 mL of 85% $H_3PO_4$ was pipetted into a 1 liter volumetric flask and diluted to volume with water and mixed thoroughly.

D. 14-Hydroxycodeinone Working Reference Standard Solutions

A stock 14-hydroxycodeinone standard solution was prepared by weighing 25±2 mg of 14-hydroxycodeinone reference material and transferring it into a 250-mL volumetric flask. Approximately 100 mL of 0.85% $H_3PO_4$ solution was added to the flask and sonicated for approximately 2 minutes or until dissolved. The solution was diluted to volume with 0.85% $H_3PO_4$ solution and mixed thoroughly. This was the stock 14-hydroxycodeinone standard solution.

A working solution of 100 ppm 14-hydroxycodeinone standard solution for system suitability was prepared by pipetting 5.0 mL of the stock 14-hydroxycodeinone standard solution into a 100-mL volumetric flask, diluting the solution to volume with water and mixing thoroughly.

A working solution of 10 ppm 14-hydroxycodeinone standard solution for sensitivity was prepared by pipetting 5.0 mL of working 100 ppm 14-hydroxycodeinone standard solution into a 50-mL volumetric flask, diluting the solution to volume with water and mixing thoroughly.

A stock hydrocodone standard solution was prepared by weighing 25±2 mg of hydrocodone reference material and transferring contents into a 250-mL volumetric flask. Approximately 100 mL of 0.85% $H_3PO_4$ solution was added to the flask and sonicated for approximately 2 minutes or until dissolved. The solution was diluted to volume with 0.85% $H_3PO_4$ solution and mixed thoroughly.

E. Hydrocodone Working Reference Standard Solution
Stock Hydrocodone Standard Solution was prepared by weighing 25±2 mg of Hydrocodone reference material and transferring contents into a 250-mL volumetric flask. Approximately 100 mL of 0.85% H3PO4 solution was added to the flask and sonicated for approximately 2 minute or until dissolved. The solution was diluted to volume with 0.85% H3PO4 Solution and mixed thoroughly.

F. Sample Solutions
A sample solution was prepared by weighing about 250 mg oxycodone API sample into a scintillation vial. 5.0 mL of water was pipetted into the vial to dissolve the sample. The vial was tightly capped and sonicated for approximately 5 minutes or until the sample was dissolved. The contents were then shaken and mixed thoroughly.

G. Resolution Test Mixture (RTM) Solution
A solution containing two components, 14-hydroxycodeinone and hydrocodone, was prepared from the respective stock standard solutions.

The Resolution Test Mixture (RTM) was prepared by pipetting separately 10.0 mL of each stock standard solution of hydrocodone above and 14-hydroxycodeinone above into the same 100 mL volumetric flask and diluted to volume with a sufficient amount of water and mixed thoroughly.

H. HPLC Conditions
The HPLC conditions were as follows:
Column: Waters, Atlantis dC18, 3×250 mm, 5 μm.

Figure 3:
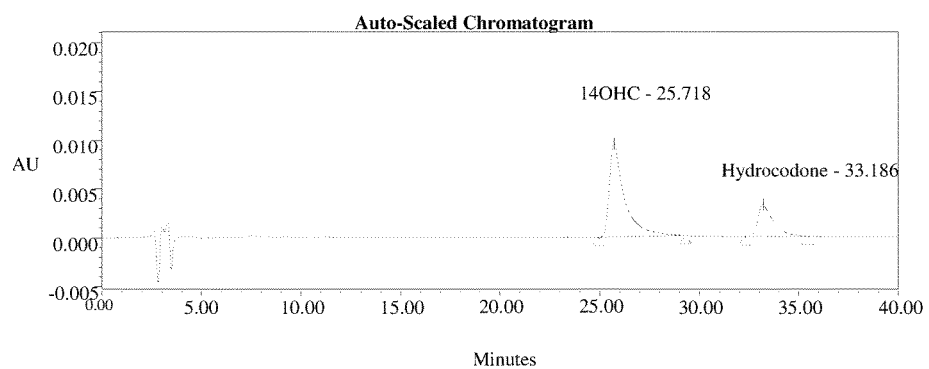
FIG. 3 depicts a separation of the system suitability testing solution of Example 4.

Column temperature: 50° C.
Detector wavelength: 220 nm
Injection volume: 6 µl
Quantitation: Peak area of 14-hydroxycodeinone
Mobile Phase: (60:40) 17 mM ammonium carbonate, pH 9.35-9.40: Methanol
Flow rate: 0.4 mL/minute
Run time: 70 minutes for the samples and 40 minutes for the standard and RTM solutions I. Resolution Test Mixture (RTM) Test Before performing the system suitability test, a new column was equilibrated over night (at least 12 hours) by pumping mobile phase through it at 0.4 mL/min. After the new column was equilibrated, 6 µL of RTM solution was injected into the equilibrated system to ensure that the two eluted component peaks did not interfere with one another. A typical separation of the system suitability testing solution is shown in FIG. 3.

J. System Suitability Test

A system suitability test was performed by injecting the Working 100 ppm 14-hydroxycodeinone standard solution into the system and by performing the system suitability test as described in the USP <621> by making six different runs of 6 µL injections. The system suitability test results met the following criteria listed in Table 1 below.

TABLE 1

| Test No. | System Suitability Test | Specification |
|---|---|---|
| 1 | RSD of peak areas for 14-hydroxycodeinone (1) | RSD ≤ 3.0% |
| 2 | RSD of retention time for 14-hydroxycodeinone (1) | RSD ≤ 2.0% |
| 3 | Column Efficiency (Theoretical Plates of 14-hydroxycodeinone) (1) | N ≥ 2000 |
| 4 | Resolution between 14-hydroxycodeinone and Hydrocodone (2) | R ≥ 1.5 |
| 5 | Signal to noise ratio (3) | S/N ≥ 10 |

Note:
(1) the working 100 ppm 14-hydroxycodeinone standard solution for Test Nos. 1 to 3 was used.
(2) the RTM for Test No. 4 was used.
(3) the working 10 ppm 14-hydroxycodeinone standard solution for Test No. 5 was used.

Before starting the experiment, 6 µL of water was injected to ensure that there were no interfering peaks co-eluting with the peak for 14-hydroxycodeinone. The following procedure was then conducted.

The working 100 ppm 14-hydroxycodeinone standard solution was injected six times in different runs, and the system was checked to verify that it met the system suitability test specifications as listed for Test Nos. 1, 2 and 3 in Table 1 above.

The RTM solution was injected and run once in the HPLC system to confirm that the system met the system suitability test specification as listed for Test No. 4 in Table 1 above.

The working 10 ppm 14-hydroxycodeinone standard solution was injected and run once in the HPLC system to confirm that the system had signal-to-noise ratio S/N greater than or equal to 10, as listed in the specification for Test No. 5 in Table 1 above.

After the system passed all of the above tests, the following HPLC procedure was performed.

The working 100 ppm 14-hydroxycodeinone standard solution and the working 10 ppm 14-hydroxycodeinone standard solution were each injected separately. Both working standard solutions were used to quantitate the samples. The setting and integration parameters are listed in Table 2 below.

TABLE 2

| Integration Setting | Parameters |
|---|---|
| Minimum area | 0 |
| Minimum height | 0 |
| Threshold | 2 |
| Peak width | 90.00 |
| Inhibit integration: 0.01 to 20 minutes | Eliminates solvent front |

Figure 4:
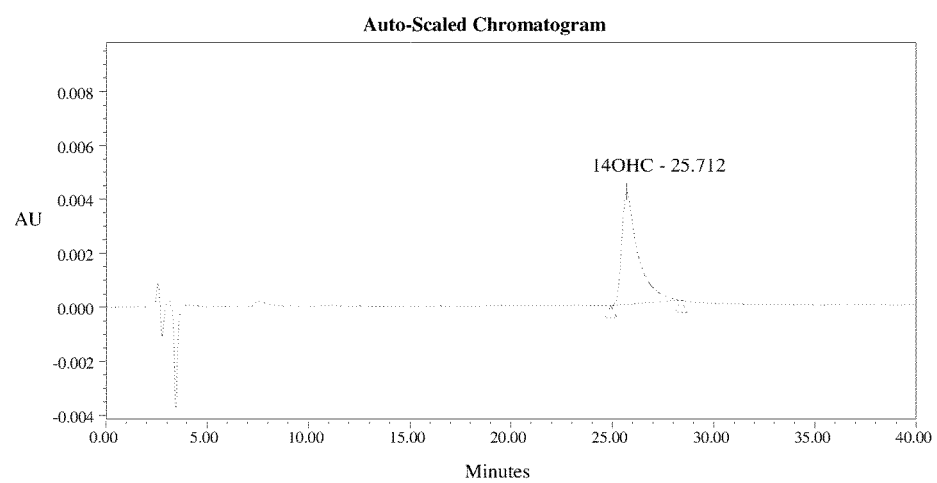
FIG. 4 depicts a HPLC chromatogram for the Working 100 PPM 14OHC Standard Solution of Example 4.
Figure 5:
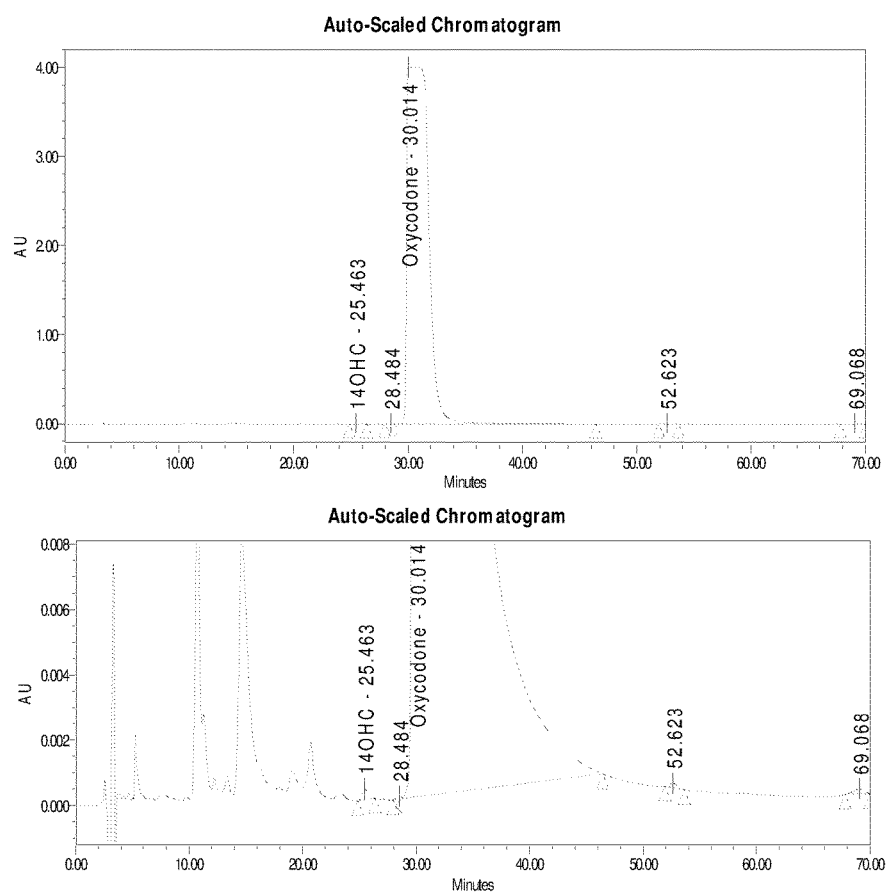
FIG. 5 depicts typical HPLC chromatogram for the Oxycodone API Sample Solution of Example 4.

Typical HPLC chromatograms for the working 100 ppm 14-hydroxycodeinone standard solution and the oxycodone API sample solution are shown in FIG. 4 and FIG. 5 respectively. Retention times of the 14-hydroxycodeinone and other related substances are presented in Table 3 below.

TABLE 3

| Peak ID | Relative Retention Time vs. Oxycodone (RRT) |
|---|---|
| Oxycodone-N-Oxide (ONO) | 0.16 |
| Noroxycodone | 0.31 |
| Oxymorphone | 0.45 |
| 7,8-Dihydro-8,14-Dihydroxycodeinone (DDC) | 0.58 |
| 14-Hydroxycodeine | 0.73 |
| 14-Hydroxycodeinone | 0.79 |
| 6-α-Oxycodol | 0.96 |
| Hydrocodone | 0.95 |
| Oxycodone | 1.0 |
| Thebaine | 1.89 |

The following calculations were performed using the results obtained above. Using Millennium®, software, the parameters were entered as follows:

In the sample set, the standard concentrations for both working standards (10 and 100 ppm) were calculated as follows:

$$100 \text{ PPM std. conc.} = \frac{W_{std} \text{corrected for purity}}{250} \times 0.05$$

$$10 \text{ PPM std. conc.} = \frac{W_{std} \text{corrected for purity}}{250} \times 0.005$$

where $W_{std}$ is the weight of standard.
The following were also entered:
  Sample weight=weight of sample in mg
  Dilution=5 ml (sample dilution)
  Label claim=0.0001 (to convert the results in PPM.
  The amount of 14-hydroxycodeinone (abbreviated as OHC) in oxycodone sample in ppm can be determined automatically from a linear calibration curve using the two standards (100 PPM and 10 PPM) and the equation used in the calculation below.

$$\text{PPM of } 14OHC = \frac{A_{sam} - Y_{intercept}}{\text{Slope}} \times \frac{D}{W_{sam}} \times 1000000$$

where:
$A_{sam}$=peak area of 14OHC
$Y_{intercept}$=Y intercept from a linear regression line using the two standards Slope=slope from a linear regression line using the two standards
D=5.0 (sample dilution factor)
$W_{sam}$=sample weight in mg
1000000=Convention factor to convert the result to PPM Example 5

3.0 g of oxycodone hydrochloric salt containing 154 ppm 14-hydroxycodeinone was dissolved in 20 mL water to afford a clear solution in a 250 mL Parr reaction bottle. To the solution, 0.05 g 5% Pd/C catalyst, 50% water wet (Johnson Matthey type 87L) and 1 mL formic acid 88% were added. The mixture was placed under inert atmosphere without hydrogen feed and then heated to 45° C.-50° C. After 2 hours of shaking, a sample was taken to check the disappearance of 14-hydroxycodeinone. The sample showed no 14-hydroxycodeinone by the HPLC method described in Example 4 above.

The solution was then suction filtered over a 0.2 micron PTFE membrane to remove the catalyst. An aliquot of 2 mL was taken out of about 18 mL filtrate solution. To this solution, 2.0 mL isopropyl alcohol was added to obtain a clear solution, followed by 4.0 mL of ethyl acetate. The solution was stirred, cooled and kept at 0-5° C. for 20 hours to afford oxycodone hydrochloride crystals. The crystalline solid was isolated by suction filtration. The wet solid was dried in an oven at 50° C. and 10 mmHg pressure. The dried solid weighed 0.12 g.

Analysis using the HPLC method in Example 4 above indicated that about 11 ppm 14-hydroxycodeinone were present in the oxycodone hydrochloride salt composition. In another aliquot of 2 mL of the filtrate solution, 16-18 mL of isopropyl alcohol was added to the concentrated oxycodone hydrochloride solution followed by crystallization and drying. The procedure afforded oxycodone hydrochloride salt containing about 6.8 ppm 14-hydroxycodeinone.

Example 6

Analysis of Sample to Determine 14-Hydroxycodeinone and Codeinone

The products of Examples 1-3 were analyzed by the following alternative method to determine the amount of codeinone and 14-hydroxycodeinone present. This method uses a Waters Symmetry $C_{18}$ column maintained at 40° C. with isocratic elution using a mobile phase of sodium phosphate buffer, sodium dodecyl sulfate (SDS), acetonitrile (ACN), and methanol (MeOH).

The reagents used were as follows:
1. Water, HPLC grade or equivalent;
2. Phosphoric acid, 85%, HPLC reagent grade or equivalent;
3. Sodium phosphate monobasic, monohydrate, Enzyme grade or equivalent;
4. Sodium dodecyl sulfate (99%+), Ultrapure, Fluka or equivalent;
5. Acetonitrile, HPLC grade or equivalent;
6. Methanol, HPLC grade or equivalent;
7. Sodium hydroxide, ACS reagent grade or equivalent;
8. Oxycodone HCl with low ABUK to be used as part of the matrix in standard preparation;
9. Codeinone reference material from Rhodes Technologies or equivalent;
10. 14-Hydroxycodeinone reference material from Albany Molecular Research or equivalent The equipment used was as follows:
A. HPLC System For this analysis, an HPLC system with a dual wavelength detector was used that was able to operate under isocratic conditions at a flow rate of 0.7 mL per minute with UV detection @ 220 nm, and a column temperature of 40° C.

B. Mobile Phase Filtration System

For this analysis, an HPLC vacuum filtration apparatus with a nylon membrane filter (0.45 μm) was used.

Solutions
i. 50% Sodium Hydroxide Solution (w/v)

50 g of sodium hydroxide pellets were weighed and transferred into a 100-mL volumetric flask. 60-mL of water was then added and sonicated until the pellets were completely dissolved. The pellets were diluted to volume with water and mixed well. (Commercially available 50% w/v NaOH solution may also be used.)

ii. Phosphoric Acid Solution I (~8.5% $H_3PO_4$)

10 ml of concentrated phosphoric acid (85%) was transferred into a 100 ml volumetric flask containing approximately 50 ml of water. The volume was diluted with water and then mixed.

iii. Phosphoric Acid Solution II (~0.85% H3PO4)

10-mL of 85% phosphoric acid was pipetted into a 1000-mL volumetric flask, diluted to volume with water and mixed well. This was the diluent for the sample and standard preparation.

iv. Mobile Phase 3.45 g±0.1 g of sodium phosphate monobasic monohydrate was weighed into a 1-L flask. 1000 mL of water was added and then stirred with a magnetic stirrer until dissolved. 5.41 g±0.1 g of sodium dodecyl sulfate was added and mixed well until dissolved. This solution was filtered using vacuum filtration with a 0.45-μm nylon membrane filter. The pH of this solution was adjusted with 50% NaOH solution to a final pH of 7.50±0.05.

722.5 ml of the above solution was then mixed with 157.5 mL of acetonitrile, then 120 mL of methanol was added to the solutions and mixed well. The final pH was adjusted to 7.80±0.01 with ~8.5% phosphoric acid solution. The mobile phase was sonicated for about 5 minutes to remove dissolved air.

i. Standard Solution Preparation Calculated Relative to Dried Samples

A. Codeinone/14-Hydroxycodeinone Stock Solution I

25±1 mg of both codeinone and 14-hydroxycodeinone reference materials were weighed and transferred into a 100-mL volumetric flask, diluted to volume and dissolved with ~0.85% phosphoric acid solution II.

ii. 100 ppm Stock Standard II 1-ml of stock solution I was pipetted into a 50-ml volumetric flask, diluted to volume with ~0.85% phosphoric acid solution II and then mixed.

iii. 10 ppm Working Standard III

500±5 mg of Oxycodone low ABUK material was weighed into a 10-ml volumetric flask. 1-ml of stock standard II was pipetted and diluted to volume with ~0.85% phosphoric acid solution II and mixed.

iv. Unspiked Oxycodone Solution

500±5 mg of Oxycodone low ABUK material was weighed into a 10-ml volumetric flask, diluted to volume with ~0.85% phosphoric acid solution II and mixed. (This solution was used to calculate the residual content of both Codeinone and 14-Hydroxycodeinone in the working standard).

E. Resolution Test Mixture (RTM)

1.0-ml of the Codeinone/14-Hydroxycodeinone stock solution I was pipetted into a 50-ml volumetric flask. Using a micropipette, 100 μl of the unspiked Oxycodone solution was transferred and diluted to volume with ~0.85% phosphoric acid solution II. The concentration of Codeinone, 14-Hydroxycodeinone, and Oxycodone was approximately 100 ppm.

F. Sample Preparations i. 50 mg/mL Oxycodone HCl Sample Solution

500±5 mg of Oxycodone HCl was weighed, in duplicate, into separate 10-mL volumetric flasks for each of Examples 1, 2 and 3. The Oxycodone HCl was then diluted to volume with the ~0.85% phosphoric acid solution II and swirled to dissolve the sample. A sufficient amount of this sample was transferred to an HPLC vial for injection.

G. HPLC Conditions

The HPLC conditions were set as follows:

TABLE 4

HPLC Conditions

| Parameter | Condition |
| --- | --- |
| HPLC Column | Symmetry $C_{18}$, 3.0 × 150 mm, 3.5 µm particle size |
| Mobile Phase | 18 mM phosphate/13 mM SDS pH = 7.50:ACN:MeOH (72.25:15.75:12.0) pH = 7.80 ± 0.01 |
| Flow Rate* | 0.7 mL/min |
| Column Temperature | 40° C. |
| Detection | 220 nm |
| Injection Volume | 5 µL |
| Run Time | 50 minutes |

*Parameter may be adjusted to achieve retention times.

H. System Suitability

One injection (5-µL) of a blank solution (~0.85% phosphoric acid solution II) was made, followed by one injection of the RTM to determine if there was any interfering peaks in the blank solution. 6 injections of the working standard III were made. The system suitability injections were then tested to verify that they met the system suitability criteria as shown in Table 2.

TABLE 5

System Suitability Criteria

| Parameter | Acceptance Criteria |
| --- | --- |
| Resolution between Codeinone and 14-Hydroxycodeinone | NLT 8 |
| Resolution between 14-Hydroxycodeinone and Oxycodone | NLT 2 |
| Tailing factor for Oxycodone | 0.7-2.0 |
| Relative retention times for Codeinone based on Oxycodone | Approx. 0.44 |
| Relative retention times for 14-Hydroxycodeinone based on Oxycodone | Approx. 0.85 |
| % RSD of 6 system suitability injections for Codeinone and 14-Hydroxycodeinone | NMT 20% |

The expected retention times were as follows:

| Components | Expected Retention Times |
| --- | --- |
| Codeinone | 14 ± 2 min |
| 14-Hydroxycodeinone | 27 ± 4 min |
| Oxycodone | 32 ± 6 min |

I. Injection Procedure

Once the column was equilibrated, the sample and standard solutions were injected according to the following sequence of Table 3:

TABLE 6

| | |
| --- | --- |
| Blank (diluent) | 1 injection |
| Resolution solution | 1 injection |
| Working Standard III | 6 injections for RSD, last 2 injections for calibration |
| Blank (diluent) | 2 injections |
| Unspiked Oxycodone solution | 2 injections |
| Sample 1 Prep# 1 | 2 injections |
| Working Standard III | 2 injections |
| Sample 1 Prep# 2 | 2 injections |
| Sample 2 Prep# 1 | 2 injections |
| Sample 2 Prep# 2 | 2 injections |
| Working Standard III | 2 injections |
| Sample 3, Prep# 1 | 2 injections |
| Sample 3, Prep# 2 | 2 injections |
| Working Standard III | 2 injections |

The Codeinone and 14-Hydroxycodeinone peaks were identified using the relative retention times as discussed above.

Calculations

The responses of Codeinone and 14-Hydroxycodeinone peaks were measured and recorded. The content of Codeinone and 14-Hydroxycodeinone was calculated in ppm using the following equation:

$$\text{ppm} = \frac{Rs \times Wstd}{Rstd \times Ws} \times \frac{1}{100} \times \frac{1}{50} \times \frac{1}{10} \times \frac{10}{1} \times \frac{1{,}000{,}000}{1}$$

$$\text{ppm} = \frac{Rs \times Wstd \times 200}{Rstd \times Ws}$$

Where:
ppm=Parts per millions of codeinone or 14-Hydroxycodeinone in Oxycodone HCl
Rs=Response of Codeinone or 14-Hydroxycodeinone in Sample Solution.
Rstd=Response of Codeinone or 14-Hydroxycodeinone in Standard Solution minus the response of unspiked standard
Wstd=Weight of Standard, corrected for purity, mg
Ws=Weight of Sample, mg
1000000=Conversion Factor for ppm % Codeinone/14-hydroxycodeinone=ppm/10,000

The results for Example 1 utilizing the procedure of Example 6 gave a result of <5 ppm of codeinone and 8 ppm of 14-hydroxycodeinone.

The results for Example 2 utilizing the procedure of Example 6 gave a result of <5 ppm of codeinone and <5 ppm of 14-hydroxycodeinone.

The results for Example 3 utilizing the procedure of Example 6 gave a result of <5 ppm of codeinone and 10 ppm of 14-hydroxycodeinone.

Many other variations of the present invention will be apparent to those skilled in the art and are meant to be within the scope of the claims appended hereto.

What is claimed is:

1. A process for preparing an oxycodone hydrochloride composition comprising, (i) reacting an oxycodone base composition with one or more acids selected from the group consisting of tartaric acid, oxalic acid, fumaric acid, phosphoric acid and sulfuric acid to form a corresponding acid addition salt of oxycodone; and (ii) converting the acid addition salt into oxycodone hydrochloride.

2. The process of claim 1, wherein step (i) comprises reacting the oxycodone base composition with sulfuric acid.

* * * * *